United States Patent
Schaare et al.

(10) Patent No.: US 9,513,156 B2
(45) Date of Patent: Dec. 6, 2016

(54) SYSTEM AND METHOD FOR DETERMINING A PROPERTY OF AN OBJECT, AND A VALVE

(71) Applicant: The New Zealand Institute for Plant and Food Research Limited, Auckland (NZ)

(72) Inventors: Peter Niven Schaare, Hamilton (NZ); Roderick Munro McDonald, Hamilton (NZ); Vincent Andrew McGlone, Hamilton (NZ)

(73) Assignee: THE NEW ZEALAND INSTITUTE FOR PLANT AND FOOD RESEA, Auckland (NZ)

( * ) Notice: Subject to any disclaimer, the term of this patent is extended or adjusted under 35 U.S.C. 154(b) by 329 days.

(21) Appl. No.: 14/379,848

(22) PCT Filed: Feb. 21, 2013

(86) PCT No.: PCT/NZ2013/000017
§ 371 (c)(1),
(2) Date: Aug. 20, 2014

(87) PCT Pub. No.: WO2014/007660
PCT Pub. Date: Jan. 9, 2014

(65) Prior Publication Data
US 2015/0059481 A1 Mar. 5, 2015

Related U.S. Application Data

(60) Provisional application No. 61/601,815, filed on Feb. 22, 2012.

(51) Int. Cl.
*F16K 3/26* (2006.01)
*G01H 9/00* (2006.01)
(Continued)

(52) U.S. Cl.
CPC .............. *G01H 3/00* (2013.01); *F16K 3/262* (2013.01); *G01H 9/00* (2013.01); *G01N 3/40* (2013.01);
(Continued)

(58) Field of Classification Search
CPC ............. F16K 3/262; G01H 3/00; G01H 9/00; G01N 3/40; G01N 33/02; G01N 2203/001; G01N 2203/0042; G01N 2203/0076
(Continued)

(56) References Cited

U.S. PATENT DOCUMENTS 3,882,718 A   5/1975  Kriebel
3,981,183 A * 9/1976  Banks ................. G01N 9/36
                                          73/32 A
(Continued)

FOREIGN PATENT DOCUMENTS

EP       318505 B1    4/1992
JP    2006038478 A    2/2006
(Continued)

OTHER PUBLICATIONS

De Ketelaere et al., Postharvest firmness changes as measured by acoustic and low-mass impact devices: a comparison of techniques, 2006.

*Primary Examiner* — J M Saint Surin
(74) *Attorney, Agent, or Firm* — Warner Norcorss and Judd LLP

(57) ABSTRACT

A system (100) for determining a property of an object (106) comprises an inducing arrangement (102), a detector (104) and a processor. The inducing arrangement (102) is configured to generate an impulse of fluid and for directing the impulse of fluid towards the object to induce a physical vibration of the object (106). The inducing arrangement
(Continued)

(102) does not contact the object 106 when inducing the physical vibration of the object (106). The detector (104) is configured to detect the physical vibration of the object (106). The detector (104) does not contact the object 106 when detecting the physical vibration of the object (106). The processor is coupled to the detector (104) for determining the property of the object (106) based on at least the detected physical vibration.

17 Claims, 30 Drawing Sheets

(51) Int. Cl.
    *G01N 3/40*     (2006.01)
    *G01N 33/02*     (2006.01)
    *G01H 3/00*     (2006.01)

(52) U.S. Cl.
    CPC ......... *G01N 33/02* (2013.01); *G01N 2203/001* (2013.01); *G01N 2203/0042* (2013.01); *G01N 2203/0076* (2013.01)

(58) Field of Classification Search
    USPC .................................... 73/655, 649; 251/326
    See application file for complete search history.

(56) References Cited

U.S. PATENT DOCUMENTS

| | | | | |
|---|---|---|---|---|
| 4,602,505 | A | * | 7/1986 | Kanda ................... G01N 11/16 73/54.26 |
| 5,251,491 | A | | 10/1993 | Nakaoka et al. |
| 5,372,030 | A | | 12/1994 | Prussia et al. |
| 6,006,593 | A | * | 12/1999 | Yamanaka ............. B82Y 35/00 73/105 |
| 6,057,927 | A | * | 5/2000 | Levesque ............... G01B 11/18 356/432 |
| 2002/0173711 | A1 | | 11/2002 | Walton |
| 2006/0054850 | A1 | | 3/2006 | Kabir et al. |
| 2011/0240894 | A1 | | 10/2011 | Yasoshima |
| 2015/0211983 | A1 | * | 7/2015 | Speck ................. G01N 21/1702 73/152.18 |
| 2015/0323385 | A1 | * | 11/2015 | Han .......................... G01J 3/36 356/300 |

FOREIGN PATENT DOCUMENTS

| | | |
|---|---|---|
| JP | 2011256893 A | 12/2011 |
| WO | 2009005426 A1 | 1/2009 |

* cited by examiner

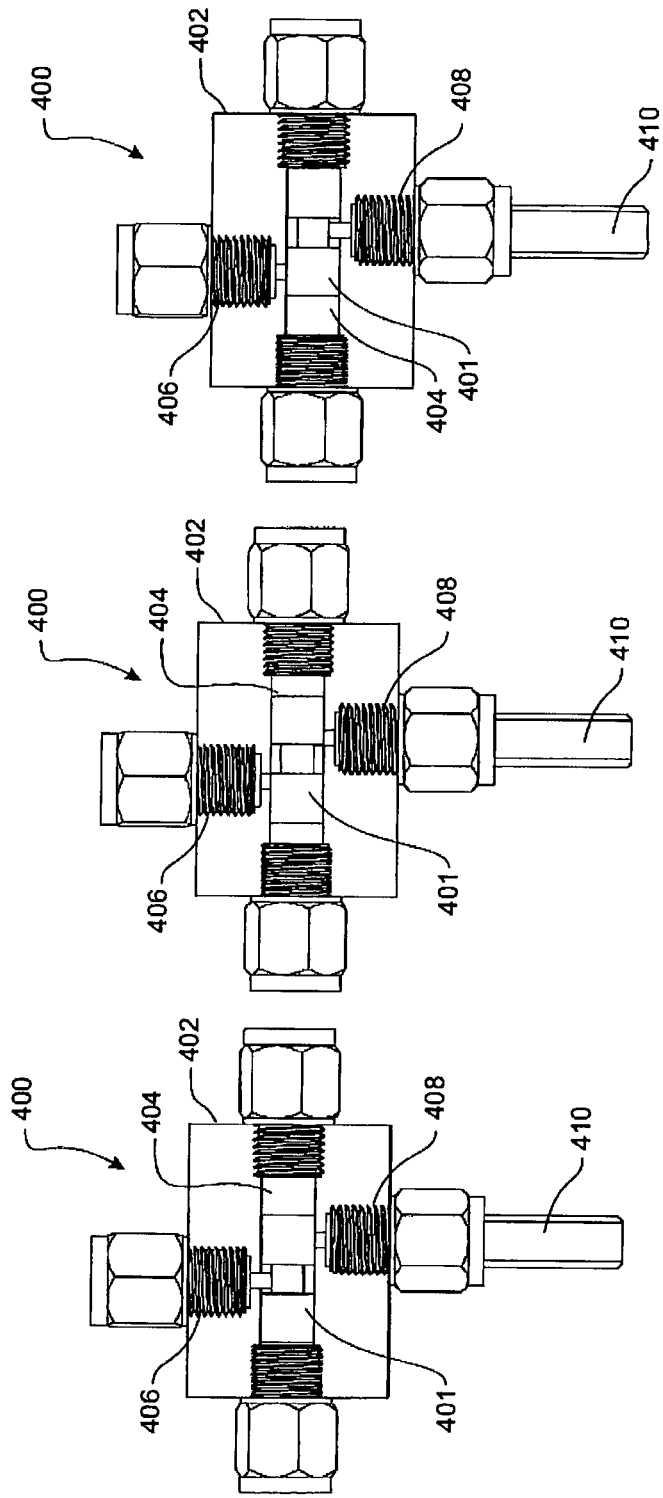

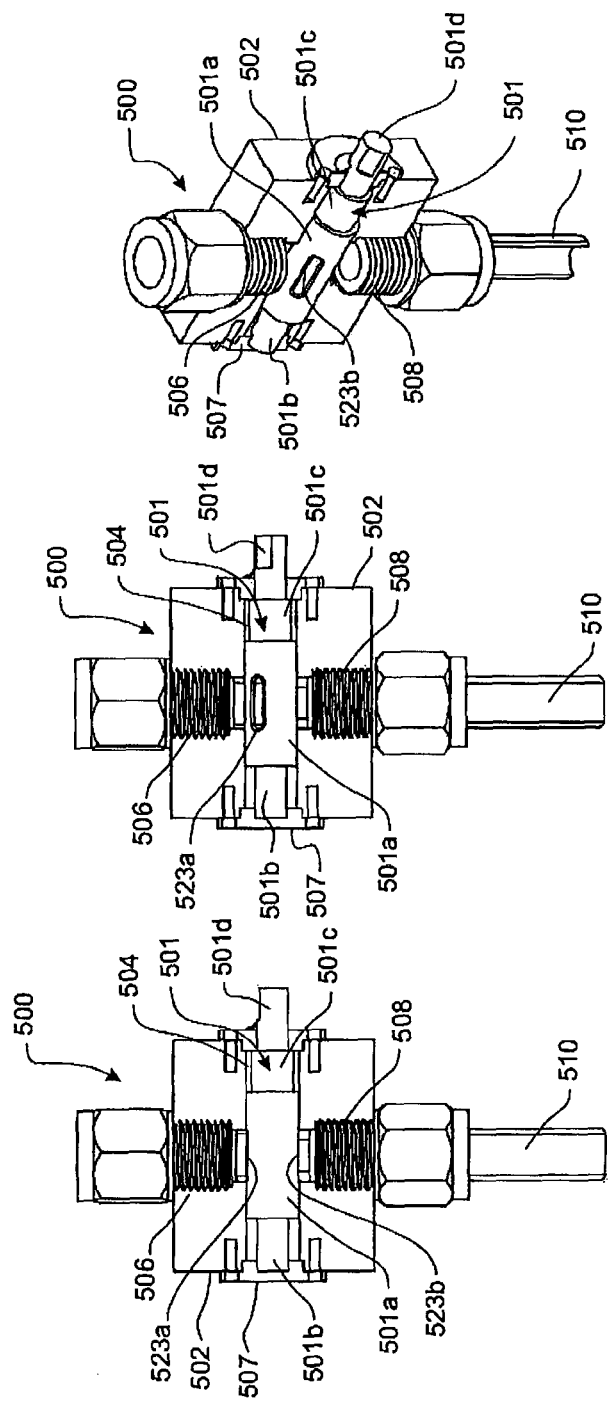

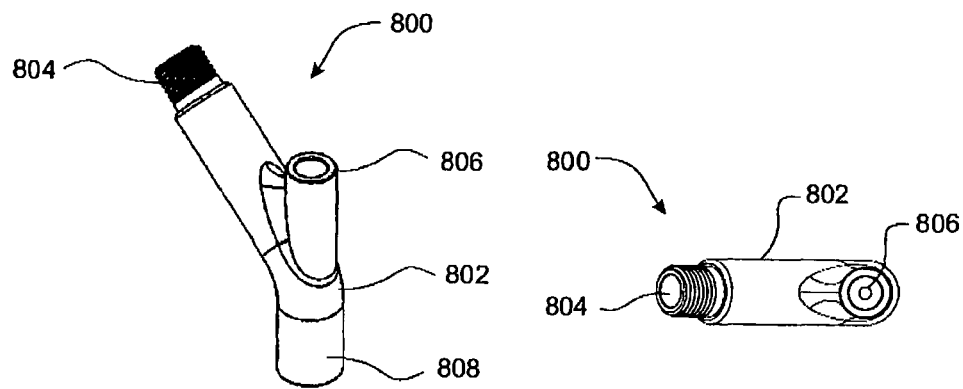
FIGURE 30A  FIGURE 30B
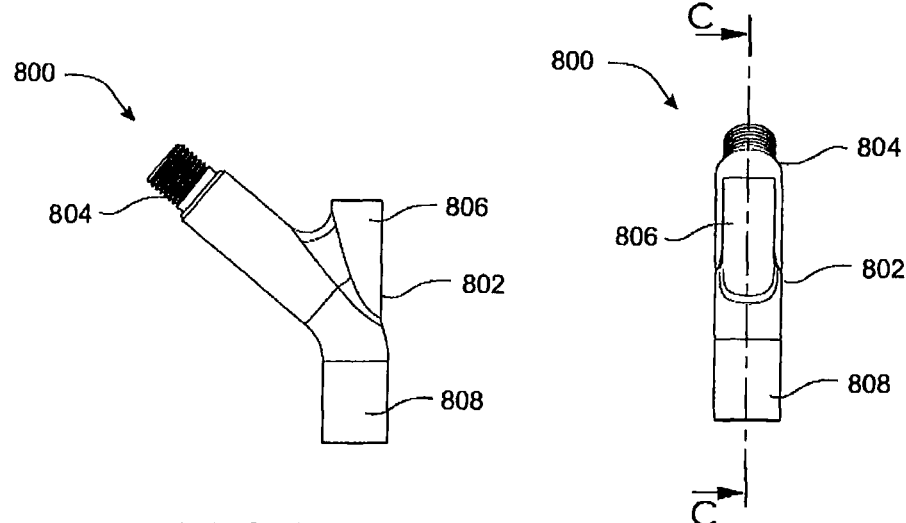
FIGURE 30C
FIGURE 30D
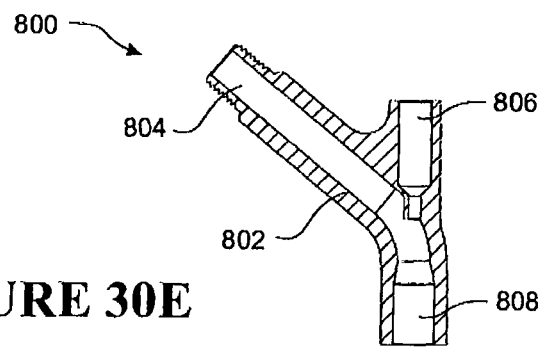
FIGURE 30E

SYSTEM AND METHOD FOR DETERMINING A PROPERTY OF AN OBJECT, AND A VALVE

FIELD OF THE INVENTION

The present invention relates to a non-destructive system and method for determining a property of an object. Embodiments of the present invention provide a system and method for determining a firmness and/or stiffness of the object. The object may be, for example, a fruit, a vegetable, meat product or any solid, hollow and/or pressurised object.

The present invention also relates to a valve which may, for example, be suitable for generating a non-destructive impulse of fluid that can be used in the non-destructive system and method of determining the object property. The valve may have other applications such as for example as a pulse echo depth gauge, a crowd control device for example.

BACKGROUND OF THE INVENTION

Automatic fruit graders are used to assess and grade whole fresh fruit and other fresh produce into different categories to create lines of fruit of consistent quality, for example of uniform size or colour. Whereas in the past produce tends to have been graded based on external properties such as size, shape, colour and external blemishes, there is now an increasing trend towards including internal qualities of produce, such as ripeness, taste and firmness, among the properties assessed by automatic graders.

The global market in horticultural grader technology is estimated to be currently $1B p.a., and increasing as world fruit production rates continue to rise. Improved grader technologies are required by fruit suppliers to handle increasing pressure coming from three separate angles. These are (i) preferred supplier status to the large supermarket chains, (ii) supplying fruit that can command a price premium and (iii) reduction in costs by minimising downgraded fruit and labour costs. A particularly strong driver for grading technology has been an increase in consumer expectations of fruit quality. Consumers increasingly expect the fruit they buy to be as consistent as manufactured foods. If a particular quality of a fresh product matters to the consumer then it is in the interest of the producer to measure, and thereby control, that quality. Retailers are responding by imposing strict grade standards, which must be met by their suppliers.

Firmness of produce (eg the 'crunchiness' of an apple) is an important factor in the consumers' selection of the produce. There are a number of existing automatic fruit graders designed to measure the firmness of individual items of fruit or produce. However, adequate solutions for determining the firmness of a fruit do not presently exist. The problems are difficult to solve since the sensor technologies must be non-destructive to the fruit, able to be integrated into existing systems without significantly reducing the overall throughput of the system, and accurate regardless of the size, presentation and morphological character of the fruit.

There are existing systems for determining the firmness of a fruit, for example the simple acoustic firmness sensor offered by Aweta, and sensors offered by Greefa and Sinclair. However, these existing systems require contact with the fruit. This requirement immediately imposes a number of constraints on the measurement, the most significant being speed but also often a considerable degree of mechanical complexity to overcome that problem. For example, the Sinclair IQ Firmness Tester uses a set of bellows to lower a firmness sensor onto fruit. The Greefa iFD uses a complex mechanical assembly to synchronise sensors with the fruit conveyor. Additionally, these existing systems are not capable of cooperating with systems which involve high speeds of conveying fruit. For example, the Greefa iFD has a maximum throughput of five fruit per second per lane.

There are generally two broad classes of grading device for measuring product firmness; the deformation method and the acoustic method. Both these methods suffer from disadvantages.

The deformation method involves measuring the response at the surface of the fruit to pressure or an impact applied at one location. This method generally requires the system to be in physical contact with the fruit. One disadvantage with the deformation method is that the system takes a measurement from a single point measurement and is therefore vulnerable to soft patches. These vulnerabilities include measuring in a soft patch and underestimating the firmness, missing a soft patch which might represent a fault, or being insensitive to broad variations around the fruit (for example being firmer on the shaded side). This disadvantage may be overcome by taking a number of measurements at different locations around the fruit. However, that approach is time consuming and reduces the throughput of the system even further. A further disadvantage with the deformation method is that such techniques may be relatively insensitive with firm fruit where deformations are small.

A system and method of implementing the deformation method using a single-point firmness measurement which does not require physical contact has been described in U.S. Pat. No. 5,372,030 (to Prussia et al). The system described in Prussia uses a jet of air to depress the surface of a fruit and a laser displacement meter to measure the resulting deformation of the fruit. The device requires large volume of pressurised air which can be commercially prohibitive. In addition, the deformation technique may be less sensitive with firm apples.

The system implementing the acoustic method uses a member to physically tap a fruit to vibrate the fruit and measures the resonant frequency of the vibration to estimate the stiffness of the fruit flesh. One disadvantage with the acoustic method is that both fruit size and shape affect the resonant frequency. Both these parameters must be known along with the resonant frequency before flesh firmness can be inferred. The size and shape of fruit are often measured by the grader and can be readily used to estimate flesh stiffness. Another disadvantage with the acoustic approach is that the sound emitted from the vibrating fruit is very small, and the acoustic pickup must be appropriately shielded from ambient noise. This must generally be done by holding the pickup against the fruit, which can be difficult to achieve in the short time available and with moving fruit. A further disadvantage with the acoustic method is that the physical tapping of the fruit can be difficult to perform, for the same reasons as for the deformation method. The speed of the fruit on the conveyor and the risk of damage to the fruit surface make it difficult to impact the fruit accurately with a physical tapper.

Manual sorting using trained operators is the only alternative means to grade for firmness and surface defects. Although accurate in some circumstances, depending on the product and/or defect, manual grading is notoriously unreliable and only economically viable in countries where suitable labour is inexpensive.

Embodiments of the present invention seek to overcome the disadvantages of the existing systems and to provide an improved system and method for non-destuctively determining a property of an object, or to at least provide the public with a useful choice. An alternative object of the present invention is to provide a valve that is suitable for delivering a short duration burst of fluid, or that at least provides the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form any part of the common general knowledge in the art.

SUMMARY OF INVENTION

In accordance with a first aspect of the present invention, there is provided a system for determining a property of an object, the system comprising:
 an inducing arrangement for generating an impulse of fluid having a duration of less than about 5 milliseconds and for directing the impulse of fluid towards the object to induce a physical vibration of the object, wherein the inducing arrangement does not contact the object when inducing the vibration of the object;
 a detector for detecting the physical vibration of the object, wherein the detector does not contact the object when detecting the physical vibration of the object; and
 a processor coupled to the detector for determining the property of the object based on at least the detected physical vibration.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in similar manner.

Preferably, the system is suitable for or configured to determine a firmness and/or stiffness property of the object.

Additionally or alternatively, the system may be suitable for or configured to determine the integrity of an object having a shell-like casing (such as for example an egg, can, bottle, or the like) to determine if the object is demarcated into different mechanical zones, cracked, fractured, and/or has surface defect(s), that is/are substantial enough to affect the resonance behaviour of the object induced by the impulse of fluid by detecting the physical vibration substantially near a defect location of the object. In one embodiment, the system may be suitable for or configured to determine the integrity of a soft-shelled container. In the case where the object is a pressurised object, the system may be used to find leak(s) in the pressurised object and/or a change in a pressurised state of the object. In one embodiment, the system may be suitable for or configured to determine a filled volume of a container.

Additionally or alternatively, the system may be suitable for or configured to determine the density, size and/or shape of the object where a firmness and/or stiffness of the object are/is known.

Preferably, the inducing arrangement is a transmitter for transmitting the impulse of fluid that impinges a surface of the object thereby inducing the physical vibration of the object. Preferably, the inducing arrangement is configured to vibrate the object at a resonant frequency.

Preferably, the inducing arrangement comprises a valve comprising:
 a housing having
  a bore,
  an inlet port, wherein fluid from a fluid source can be delivered into the bore through the inlet port, and
  an outlet port, wherein fluid from within the bore can be delivered through the outlet port; and
 a valve member moveable within the bore of the housing between a first substantially closed configuration, an open configuration, and a second substantially closed configuration, wherein in the open configuration, the valve member substantially allows fluid flow from the inlet port to the outlet port, and in the first and second substantially closed configurations, the valve member substantially restricts fluid flow from the inlet port to the outlet port, the valve member being moveable from one of the substantially closed configurations to the open configuration to the other substantially closed configuration in a single direction of motion of the valve member within the bore.

Preferably, the valve member is a reciprocable spool valve member, and the spool valve member is moveable from one of the substantially closed configurations to the open configuration to the other substantially closed configuration in a single linear stroke of the spool valve member within the bore. Preferably, the spool valve member has two restricting sections, each restricting section being dimensioned to substantially restrict fluid flow from the inlet port to the outlet port when the spool valve member is in either of the substantially closed configurations, and a delivery section located in between the two restricting sections, the delivery section being dimensioned to substantially allow fluid flow from the inlet port to the outlet port when the spool valve member is in the open configuration.

Alternatively, the valve member is a rotatable spool valve member, and the rotatable spool valve member is moveable from one of the substantially closed configurations to the open configuration to the other substantially closed configuration in a single rotation of the rotatable spool valve member within the bore.

Preferably, the inlet port and the outlet port are substantially opposite one another. Preferably, the inlet port and the outlet port are directly opposite one another. Alternatively, the inlet port may be offset from the outlet port. Preferably, a direction of fluid into the inlet port is substantially parallel to a direction of fluid from the outlet port. Alternatively, the inlet port may be at a non-parallel angle relative to the outlet port, wherein a direction of fluid into the inlet port is at a non-parallel angle to a direction of fluid from the outlet port. Preferably, the outlet port is angled relative to the inlet port such that the direction of fluid from the outlet port is at an angle of between about 90° and about 180° from the direction of fluid into the inlet port. Preferably, the outlet port is angled relative to the inlet port such that the direction of fluid from the outlet port is at an angle of about 130° from the direction of fluid into the inlet port.

Preferably, a movement of the valve member from one of the substantially closed configurations to the open configuration to the other substantially closed configuration in the single direction of motion within the bore takes about 30 milliseconds to about 70 milliseconds. Preferably, the movement of the valve member from one of the substantially closed configurations to the open configuration to the other substantially closed configuration in the single direction of motion takes about 50 milliseconds.

Preferably, the inducing arrangement further comprises a driving arrangement for driving the valve member within the bore from one of the substantially closed configurations to the open configuration to the other substantially closed configuration.

Preferably, in the embodiment with a reciprocable spool valve member, the spool valve member is pneumatically driven and the driving arrangement is a pneumatic valve connected to at least one end of the bore. The driving arrangement may alternatively be a solenoid. Alternatively, the driving arrangement may be a mechanical apparatus to mechanically reciprocate the spool valve member. The mechanical apparatus may include a motorised push rod or cam. The mechanical apparatus may comprise a spring to return the valve in one direction after it has been driven either pneumatically or mechanically in the other direction.

Preferably, the inducing arrangement is arranged to generate an impulse of fluid through the outlet port, the duration of the impulse corresponding to an amount of time the spool valve member remains in the open configuration during the stroke. Preferably, the impulse of fluid has a substantially short duration. Preferably, the duration of the impulse of fluid is less than about 3 milliseconds. Preferably, the duration of the impulse of fluid is about 1 millisecond.

Preferably, the impulse of fluid has a direction of propagation towards the object substantially perpendicular to a direction of signals communicated between the detector and the object. Preferably, the inducing arrangement is horizontally spaced from the object being measured, such that the impulse of fluid from the inducing arrangement impinges a side surface of the object. Alternatively, the inducing arrangement may be vertically spaced from the object being measured such that the impulse of fluid from the inducing arrangement impinges a top surface of the object. Preferably, the inducing arrangement is spaced by more than about 1 mm from the object being measured. Preferably, the inducing arrangement is spaced by about 10 mm to about 500 mm from the object being measured. Preferably, the inducing arrangement is spaced by about 50 mm to about 200 mm from the object being measured.

Alternatively, the impulse of fluid may have a direction of propagation towards the object that is generally coincident to a direction of signals communicated between the detector and the object. Preferably, the direction of propagation and the direction of signals are generally coincident with each other on the object. Preferably, the direction of propagation and the direction of signals are generally coincident with each other on a top surface of the object.

Preferably, the system comprises an impulse guide for directing the impulse of fluid from the inducing arrangement and for directing the signals between the detector and the object in a same direction towards the object. Preferably, the impulse guide comprises a body having a first arm through which the impulse of fluid from the inducing arrangement is to be directed, a second arm through which signals are to be communicated between the detector and the object, and a third arm in communication with the first and second arms, wherein the impulse of fluid received by the first arm is configured to pass through the first arm and the third arm toward the object and signals between the detector and object are configured to pass through the second arm and the third arm. Preferably, the first arm is at an angle of between about 90° and about 180° to the second arm. Preferably, the first arm is at an angle of about 130° to the second arm. Alternatively, the first arm may be substantially perpendicular to the second arm. Preferably, the third arm is substantially collinear with the second arm. Alternatively, the third arm may be substantially collinear with the first arm. Preferably, the impulse guide is separate from the inducing arrangement. Alternatively, the impulse guide may be integral with the inducing arrangement.

Preferably, the fluid is substantially inert or benign. Preferably, the fluid is a gas. Alternatively, the fluid may be a liquid or a mixture of liquid and gas. Alternatively, the fluid may be a mixture of gas and one or more powdered solids. Preferably, the impulse of gas is pressurised air. Preferably, the gas is pressurised to between about 0.2 MPa and about 3.0 MPa.

Preferably, the detector comprises a laser-based detector. Preferably, the detector comprises a laser Doppler vibrometer (LDV) arranged to transmit signals to and receive signals from the object. Preferably, the detector comprises an optical guide for selectively communicating signals between the detector and the object on one of a plurality of conveyors, each conveyor being adapted to convey a series of objects. Preferably, in the case where a plurality of conveyors is present, the system comprises a plurality of inducing arrangements, each inducing arrangement being assigned to one of the plurality of conveyors. Preferably, the optical guide is an electronically-movable deflection mirror.

Preferably, signals between the detector and the object have a direction substantially perpendicular to a movement direction of the object being conveyed. Preferably, the direction of the signals between the detector and the object is between about 89.5° and about 90.5° to a direction of movement of the object being conveyed. Preferably, the direction of the signals between the detector and the object is substantially 90° to a direction of movement of the object being conveyed.

Preferably, the system is configured to determine the property of more than about five objects per second. Preferably, the system is configured to determine the property of about ten objects per second. Preferably, the system is configured to determine the property of about fifteen objects per second. In a multiple-conveyor or lane configuration, the system is preferably configured to determine the property of the stated number of objects per second per conveyor or lane.

In accordance with a second aspect of the present invention, there is provided a method for determining a property of an object, the method comprising:
  inducing by an inducing arrangement a physical vibration of the object, the inducing arrangement being configured to generate an impulse of fluid having a duration of less than about 5 milliseconds and to direct the impulse of fluid towards the object,
  wherein the inducing arrangement does not contact the object when inducing a vibration of the object;
  detecting by a detector the physical vibration of the object, wherein the detector does not contact the object when detecting the vibration; and
  determining the property of the object based on at least the detected physical vibration.

Preferably, the method comprises determining a firmness and/or stiffness property of an object.

Additionally or alternatively, the method may comprise determining the integrity of an object having a shell-like casing (such as for example an egg, can, bottle, or the like) to determine if the object is demarcated into different mechanical zones, cracked, fractured, and/or has surface defect(s), that is/are substantial enough to affect the resonance behaviour of the object induced by the impulse of fluid by detecting the physical vibration substantially near a defect location of the object. In one embodiment, the method comprises determining the integrity of a soft-shelled container. In the case where the object is a pressurised object, the method may be used to find leak(s) in the pressurised object and/or a change in a pressurised state of the object. In one embodiment, the method comprises determining a filled volume of a container.

Additionally or alternatively, the method may comprise determining the density, size and/or shape of the object where a firmness and/or stiffness of the object is/are known.

Preferably, the inducing arrangement is a transmitter, and the method comprises transmitting, using the transmitter, the impulse of fluid that impinges a surface of the object thereby inducing the physical vibration of the object. Preferably, method comprises vibrating, using the inducing arrangement, the object at a resonant frequency.

Preferably, the inducing arrangement comprises a valve comprising
a housing having
a bore,
an inlet port, wherein fluid from a fluid source can be delivered into the bore through the inlet port, and
an outlet port, wherein fluid from within the bore can be delivered through the outlet port; and
a valve member moveable within the bore of the housing between a first substantially closed configuration, an open configuration, and a second substantially closed configuration, wherein in the open configuration, the valve member substantially allows fluid flow from the inlet port to the outlet port, and in the first and second substantially closed configurations, the valve member substantially restricts fluid flow from the inlet port to the outlet port, the spool valve member being moveable from one of the substantially closed configurations to the open configuration to the other substantially closed configuration in a single direction of motion of the valve member within the bore.

Preferably, the valve member is a reciprocable spool valve member, and the method comprises moving the spool valve member from one of the substantially closed configurations to the open configuration to the other substantially closed configuration in a single linear stroke of the spool valve member within the bore. Preferably, the spool valve member has two restricting sections, each restricting section being dimensioned to substantially restrict fluid flow from the inlet port to the outlet port when the spool valve member is in either of the substantially closed configurations, and a delivery section located in between the two restricting sections, the delivery section being dimensioned to substantially allow fluid flow from the inlet port to the outlet port when the spool valve member is in the open configuration.

Alternatively, the valve member may be a rotatable spool valve member, and the method comprises rotating the rotatable spool valve member from one of the substantially closed configurations to the open configuration to the other substantially closed configuration in a single rotation of the rotatable spool valve member within the bore.

Preferably, the inlet port and the outlet port are substantially opposite from one another. Preferably, the inlet port and the outlet port are directly opposite one another. Alternatively, the inlet port may be offset from the outlet port. Preferably, the method comprises directing fluid into the inlet port in a direction that is substantially parallel with a direction of fluid from the outlet port. Alternatively, the inlet port may be at a non-parallel angle relative to the outlet port, and the method comprises directing fluid into the inlet port at a non-parallel angle to a direction of fluid from the outlet port. Preferably, the outlet port is angled relative to the inlet port such that the direction of fluid from the outlet port is at an angle of between about 90° and about 180° from the direction of fluid into the inlet port. Preferably, the outlet port is angled relative to the inlet port such that the direction of fluid from the outlet port is at an angle of about 130° offset from the direction of fluid into the inlet port.

Preferably, the method comprises generating, using the inducing arrangement, an impulse of fluid through the outlet port, the duration of the impulse corresponding to an amount of time the valve member remains in the open configuration during the stroke. Preferably, the impulse of fluid has a substantially short duration. Preferably, the duration of the impulse of fluid is less than about 3 milliseconds, Preferably, the duration of the impulse of fluid is about 1 millisecond.

Preferably, the method comprises directing the impulse of fluid in a direction of propagation towards the object that is substantially perpendicular to a direction of signals communicated between the detector and the object. Preferably, the inducing arrangement is horizontally spaced from the object being measured, and the method comprises directing the impulse of fluid from the inducing arrangement to impinge a side surface of the object. Alternatively, the inducing arrangement is vertically spaced from the object being measured, and the method comprises directing the impulse of fluid from the inducing arrangement to impinge a top surface of the object. Preferably, the inducing arrangement is spaced by more than about 1 mm from the object being measured. Preferably, the inducing arrangement is spaced by about 10 mm to about 500 mm from the object being measured. Preferably, the inducing arrangement is spaced by about 50 mm to about 200 mm from the object being measured.

Alternatively, the method comprises directing the impulse of fluid in a direction of propagation towards the object that is generally coincident to a direction of signals communicated between the detector and the object. Preferably, method comprises directing the impulse of fluid such that the direction of propagation and the direction of signals are generally coincident with each other on the object. Preferably, the method comprises directing the impulse of fluid such that the direction of propagation and the direction of signals are generally coincident with each other on a top surface of the object.

Preferably, the method comprises directing the impulse of fluid from the inducing arrangement and the signals between the detector and the object in a same direction towards the object using an impulse guide. Preferably, the impulse guide comprises a body having first arm through which the impulse of fluid from the inducing arrangement is directed, a second arm through which signals are communicated between the detector and the object, and a third arm in communication with the first and second arms, wherein the method comprises passing the impulse of fluid through the first arm and the third arm toward the object and passing signals between the detector and object through the second arm and the third arm. Preferably, the first arm is at an angle of between about 90° and about 180° to the second arm. Preferably, the first arm is at an angle of about 130° to the second arm. Alternatively, the first arm may be substantially perpendicular to the second arm. Preferably, the third arm is substantially collinear with the second arm. Alternatively, the third arm may be substantially collinear with the first arm. Preferably, the impulse guide is separate from the inducing arrangement. Alternatively, the impulse guide may be integral with the inducing arrangement.

Preferably, the fluid is substantially inert or benign. Preferably, the fluid is a gas. Alternatively, the fluid may be a liquid or a mixture of liquid and gas. Alternatively, the fluid may be a mixture of gas and one or more powdered solids. Preferably, the impulse of fluid is pressurised air. Preferably, the gas is pressurised to between about 0.2 MPa and about 3.0 MPa.

Preferably, the detector comprises a laser-based detector. Preferably, the detector comprises a laser Doppler vibrometer (LDV), and the method comprises transmitting signals to and receiving signals from the object using the LDV. Preferably, the detector comprises an optical guide, and the method comprises selectively communicating signals between the detector and the object on one of a plurality of conveyors using the optical guide, each conveyor being adapted to convey a series of objects. Preferably, in the case where a plurality of conveyors is present, the system comprises a plurality of inducing arrangements, each inducing arrangement being assigned to one of the plurality of conveyors. Preferably, the optical guide is an electronically-movable deflection mirror.

Preferably, the method comprises directing signals between the detector and the object in a direction substantially perpendicular to a movement direction of the object being conveyed. Preferably, the method comprises directing the signals between the detector and the object at an angle between about 89.5 and about 90.5° to a direction of movement of the object being conveyed. Preferably, the method comprises directing the signals between the detector and the object at an angle of substantially 90° to a direction of movement of the object being conveyed.

Preferably, the method comprises determining the property of more than about five objects per second. Preferably, the method comprises determining the property of about ten objects per second. Preferably, the method comprises determining the property of about fifteen objects per second. In a multiple-conveyor or lane configuration, the method preferably comprises determining the property of the stated number of objects per second per conveyor or lane.

In accordance with a third aspect of the present invention, there is provided a valve comprising:
  a housing having
    a bore,
    an inlet port, wherein fluid from a fluid source can be delivered into the bore through the inlet port, and
    an outlet port substantially close to the inlet port, wherein fluid from within the bore can be delivered through the outlet port; and
  a valve member moveable within the bore of the housing between a first substantially closed configuration, an open configuration, and a second substantially closed configuration, wherein in the open configuration, the valve member substantially allows fluid flow from the inlet port to the outlet port, and in the first and second substantially closed configurations, the valve member substantially restricts fluid flow from the inlet port to the outlet port, the valve member being moveable from one of the substantially closed configurations to the open configuration to the other substantially closed configuration in a single direction of motion of the valve member within the bore to generate an impulse of fluid through the outlet port having a duration of less than about 5 milliseconds.

Preferably, the duration of the impulse is less than about 3 milliseconds. Preferably, the duration of the impulse is about 1 millisecond.

Preferably, the valve member is a reciprocable spool valve member, and the spool valve member is moveable from one of the substantially closed configurations to the open configuration to the other substantially closed configuration in a single linear stroke of the spool valve member within the bore. Preferably, the spool valve member has two restricting sections, each restricting section being dimensioned to substantially restrict fluid flow from the inlet port to the outlet port when the spool valve member is in either of the substantially closed configurations, and a delivery section located in between the two restricting sections, the delivery section being dimensioned to substantially allow fluid flow from the inlet port to the outlet port when the spool valve member is in the open configuration.

Alternatively, the valve member may be a rotatable spool valve member, and the rotatable spool valve member is moveable from one of the substantially closed configurations to the open configuration to the other substantially closed configuration in a single rotation of the rotatable spool valve member within the bore.

Preferably, the inlet port and the outlet port are substantially opposite one another. Preferably, the inlet port and the outlet port are directly opposite one another. Alternatively, the inlet port may be offset from the outlet port.

Preferably, a movement of the valve member from one of the substantially closed configurations to the open configuration to the other substantially closed configuration in the single direction of motion within the bore takes about 30 milliseconds to about 70 milliseconds. Preferably, the movement of the valve member from one of the substantially closed configurations to the open configuration to the other substantially closed configuration in the single direction of motion takes about 50 milliseconds.

Preferably, the valve further comprises a driving arrangement for driving the valve member within the bore from one of the substantially closed configurations to the open configuration to the other substantially closed configuration.

Preferably, in the embodiment having a reciprocable spool valve member, the spool valve member is pneumatically driven and the driving arrangement is a pneumatic valve connected to at least one end of the bore. The driving arrangement may be a solenoid. Alternatively, the driving arrangement may be a mechanical apparatus to mechanically reciprocate the spool valve member.

In accordance with the fourth aspect of the present invention, there is provided a valve comprising:
  a housing having
    a bore,
    an inlet port, wherein fluid from a fluid source can be delivered into the bore through the inlet port, and
    an outlet port substantially close to the inlet port, wherein fluid from within the bore can be delivered through the outlet port; and
  a reciprocable spool valve member moveable within the bore of the housing between a first substantially closed configuration, an open configuration, and a second substantially closed configuration, the spool valve member being moveable from one of the substantially closed configurations to the open configuration to the other substantially closed configuration in a single linear direction of motion of the spool valve member within the bore, the spool valve member having
    two restricting sections, each restricting section being dimensioned to substantially restrict fluid flow from the inlet port to the outlet port when the spool valve member is in either of the substantially closed configurations, and a delivery section located in between the two restricting sections, the delivery section being dimensioned to generate an impulse of fluid through the outlet port in a single stroke of the spool valve member in the bore, the impulse having a duration corresponding to an amount of time the spool valve member remains in the open configuration during the stroke.

Preferably, the inlet port and the outlet port are substantially opposite one another. Preferably, the inlet port and the outlet port are directly opposite one another. Alternatively, the inlet port may be offset from the outlet port.

Preferably, the single stroke of the spool valve member within the bore takes about 30 milliseconds to about 70 milliseconds. Preferably, the single stroke of the spool valve member takes about 50 milliseconds.

Preferably, the valve further comprises a driving arrangement for driving the spool valve member within the bore from one of the substantially closed configurations to the open configuration to the other substantially closed configuration.

Preferably, the spool valve member is pneumatically driven and the driving arrangement is a pneumatic valve connected to at least one end of the bore. The driving arrangement may be a solenoid. Alternatively, the driving arrangement may be a mechanical apparatus to mechanically reciprocate the spool valve member.

Preferably, the valve is arranged to generate an impulse of fluid through the outlet port in a single stroke of the spool valve member in the bore, the impulse having a duration corresponding to an amount of time the spool valve member remains in the open configuration during the stroke. Preferably, the impulse has a substantially short duration. Preferably, the duration of the impulse is less than about 5 milliseconds. Preferably, the duration of the impulse is less than about 3 milliseconds. Preferably, the duration of the impulse is about 1 millisecond.

Preferably, the inducing arrangement of the system according to the first aspect of the invention and method according to the second aspect of the invention comprise either of the valves according to the third or fourth aspects of the invention. Alternatively, the valves may be used in other applications such as, for example, in a stress-wave velocity measurement system, in a pulse echo system, or in a crowd control device.

Where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

The present invention will now be described by way of non-limiting example only and with reference to the accompanying drawings in which:

FIG. 10 shows a front sectional view of the inducing arrangement according to an alternative embodiment of the present invention when the spool valve member is in the first substantially closed configuration;

FIG. 11 shows a front sectional view of the inducing arrangement shown in FIG. 10 when the spool valve member is in the open configuration;

FIG. 12 shows a front sectional view of the inducing arrangement shown in FIG. 10 when the spool valve member is in the second substantially closed configuration;

FIG. 15 shows a front sectional view of an inducing arrangement according to another alternative embodiment of the present invention when the spool valve member is in the open configuration;

FIG. 16 shows a front sectional view of the inducing arrangement shown in FIG. 15 when the spool valve member is in a first substantially closed configuration;

FIG. 17 is a perspective sectional view of the inducing arrangement shown in FIG. 15 when the spool valve member is in a second substantially closed configuration;

FIG. 30A shows a perspective view of an impulse guide according to a second embodiment of the invention for the system shown in FIG. 26;

FIG. 30B shows a top view of the impulse guide shown in FIG. 30A;

FIG. 30C shows a front view of the impulse guide shown in FIG. 30A;

FIG. 30D shows a side view of the impulse guide shown in FIG. 30A;

FIG. 30E shows a sectional front view of the impulse guide shown in FIG. 30A taken along the lines C-C of FIG. 30D;

DETAILED DESCRIPTION OF PREFERRED EMBODIMENTS

Figure 1:
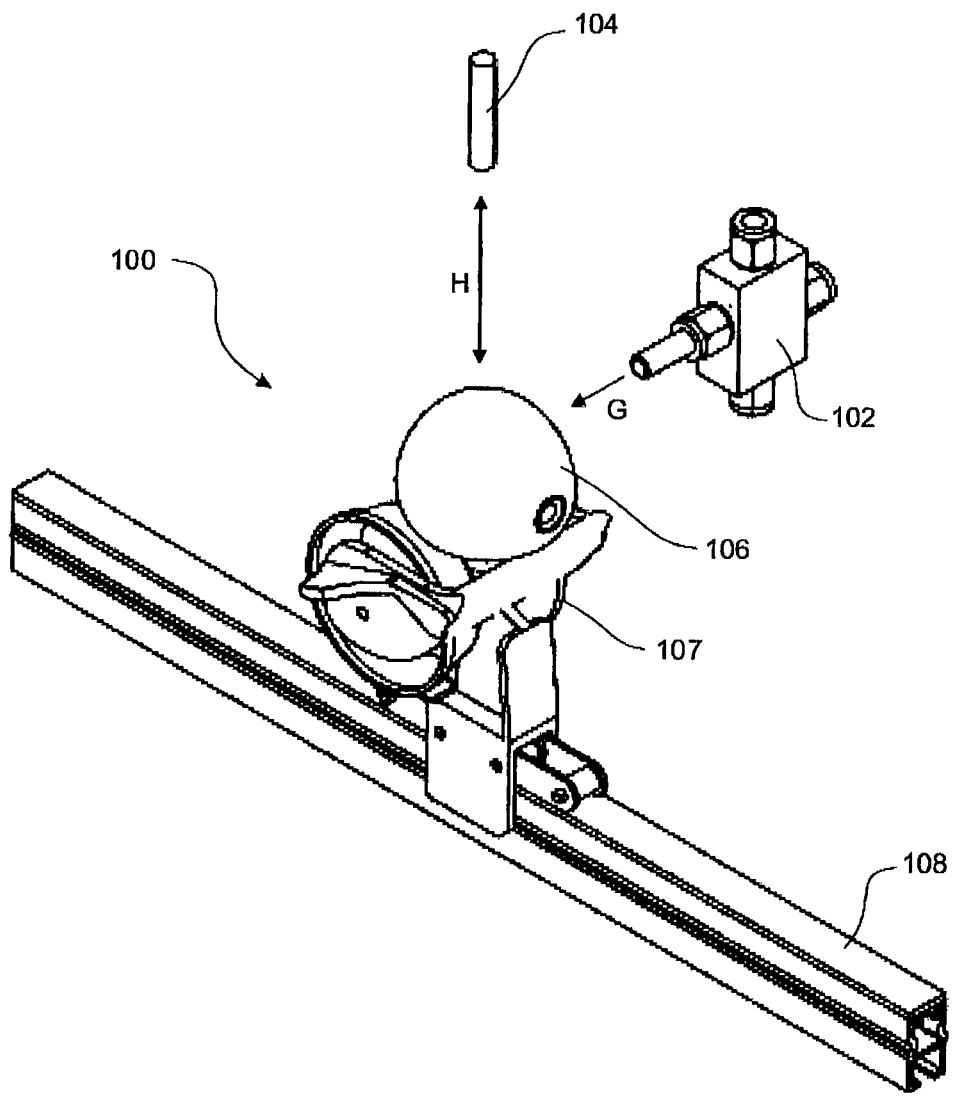
FIG. 1 shows a perspective view of the system of an embodiment of the present invention.
Figure 2:
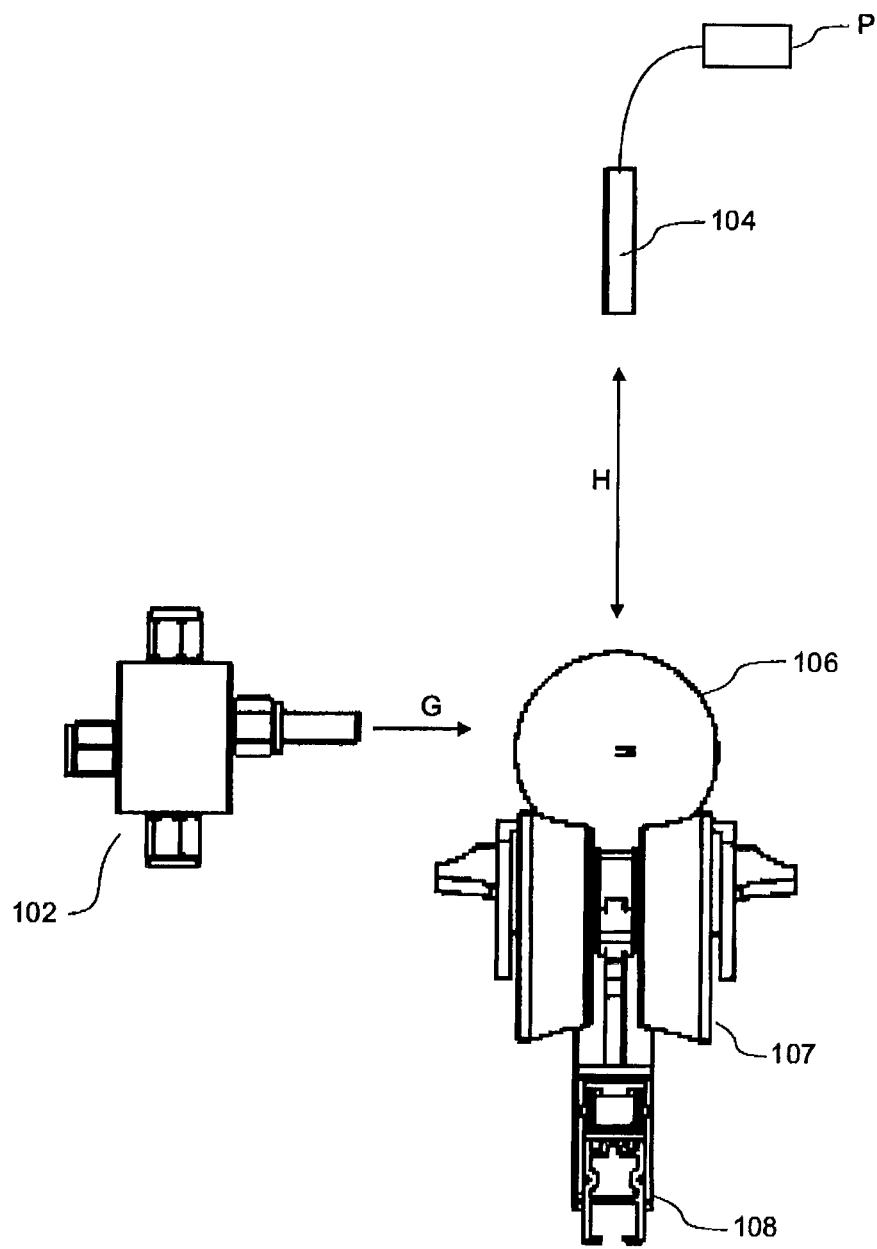
FIG. 2 shows a front view of the system shown in FIG. 1.
Figure 3:
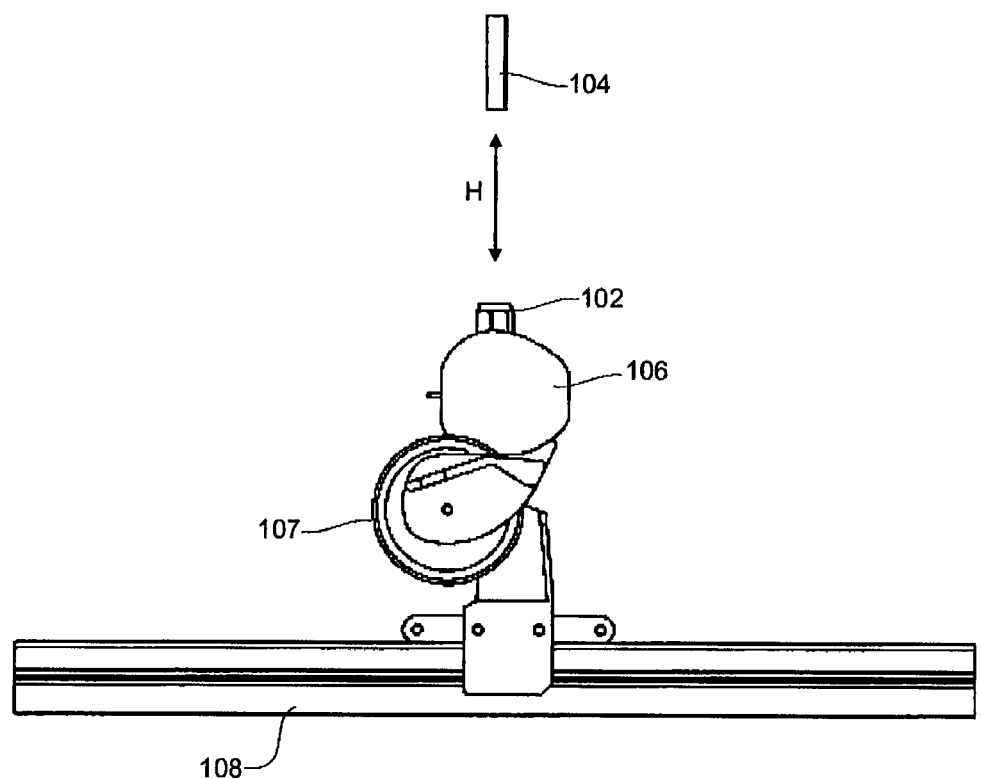
FIG. 3 shows a side view of the system shown in FIG. 1.

FIGS. 1 to 3 show the system 100 for determining a property of an object 106 according to an embodiment of the present invention. For the embodiment described, the object 106 under inspection is a fruit (for example, apples, peaches, avocados, and kiwifruit). However, it should be understood that the object 106 could be any other object such as a vegetable (such as a potato), meat products (such as fish fillets) or any solid, hollow and/or pressurised object. In particular, the object 106 may be any object with a quality that depends on structural stiffness, firmness, elasticity and/or internal pressure (skin/drum effect). The object 106 may be a soft-shelled container. The object 106 may be a glass bottle, pressurised can or tank (such as a gas tank). The system 100 may be applied on pressurised sporting goods (for example balls with stiff rubberised shells like tennis balls, squash balls, and the like). The system could also be used on eggs. In that case, the resonance behaviour will change greatly depending on the condition of the yolk or integrity of the shell.

The system 100 is particularly configured to determine a firmness property of an object 106 such as a fruit in a holder 107 that is conveyed down a conveyor line 108. Additionally or alternatively, the system 100 may be used to determine the integrity of an object 106 having a shell-like casing (such as for example and egg, can, bottle, or the like) to determine if the object 106 is demarcated into different mechanical zones, cracked, fractured, and/or has surface defect(s). The system 100 may be used to detect if the object 106 has different mechanical zones, crack(s), fracture(s), and/or surface defect(s), that is/are substantial enough to affect the resonance behaviour of the object 106 induced by the impulse of fluid. In the case where the object 106 is rigid, the system 100 can determine the integrity of the objects 106 provided that the measurements are taken close to the defect site. In the case where the object 106 is a pressurised object, the system 100 may be used to find leak(s) in the pressurised object and/or to determine a change in a pressurised state of the object 106. Additionally or alternatively, the system 100 may be used to determine the density, size and/or shape of the object 106 where a firmness of the object 106 is known. Additionally or alternatively, the system 100 may be suitable for or configured to determine a filled volume of a container.

The system 100 generally comprises an inducing arrangement 102 and a detector 104. The system 100 additionally comprises a processor P (shown in FIG. 2) that is coupled to the detector 104. The processor P is configured to determine the property of the object 106 based on measurements received from the detector 104.

The system 100 determines the firmness of the object by impacting a short, sharp burst of compressed air generated by the inducing arrangement 102 onto the object 106 along a first path G and sensing (or detecting), by the detector 104 along a second path H, the resulting vibrations of the object 106. The first path G is substantially perpendicular to the second path H. Further, the first path G and second path H are substantially linear. According to alternative embodiments, the first path may be parallel to the second path, or the first path and/or the second path may be substantially non-linear between the inducing arrangement 102 or detector 104 respectively and the object 106. Throughout the process, the inducing arrangement 102 and the detector 104 do not physically contact the object 106 being measured. This method is referred to generally hereinafter as the 'Fluid Tap' method.

Using air (or any other gas, liquid or mixture of liquid and air) jet(s) for rapid and robust mechanical force coupling and non-contact optical sensor(s) for fast response measurements, the system is able to achieve fast grading speeds, in excess of ten objects per second.

The inducing arrangement 102, the detector 104, and the processor P will be described in further detail below.

The Inducing Arrangement

Still referring to FIGS. 1 to 3, the function of the inducing arrangement 102 is to generate an impulse of fluid and to direct the impulse of fluid towards the object 106 to induce a physical vibration in the object 106. The inducing arrangement 102 does not physically contact the object 106 when inducing the vibration in the object 106. The impulse of fluid is pressurised air having a short duration. Besides pressurised air, the impulse of fluid may be an impulse comprising a substantially inert or benign fluid. The fluid may be a gas, a liquid, a mixture of liquid and gas, or alternatively a mixture of gas and one or more powdered solids.

Figure 4:
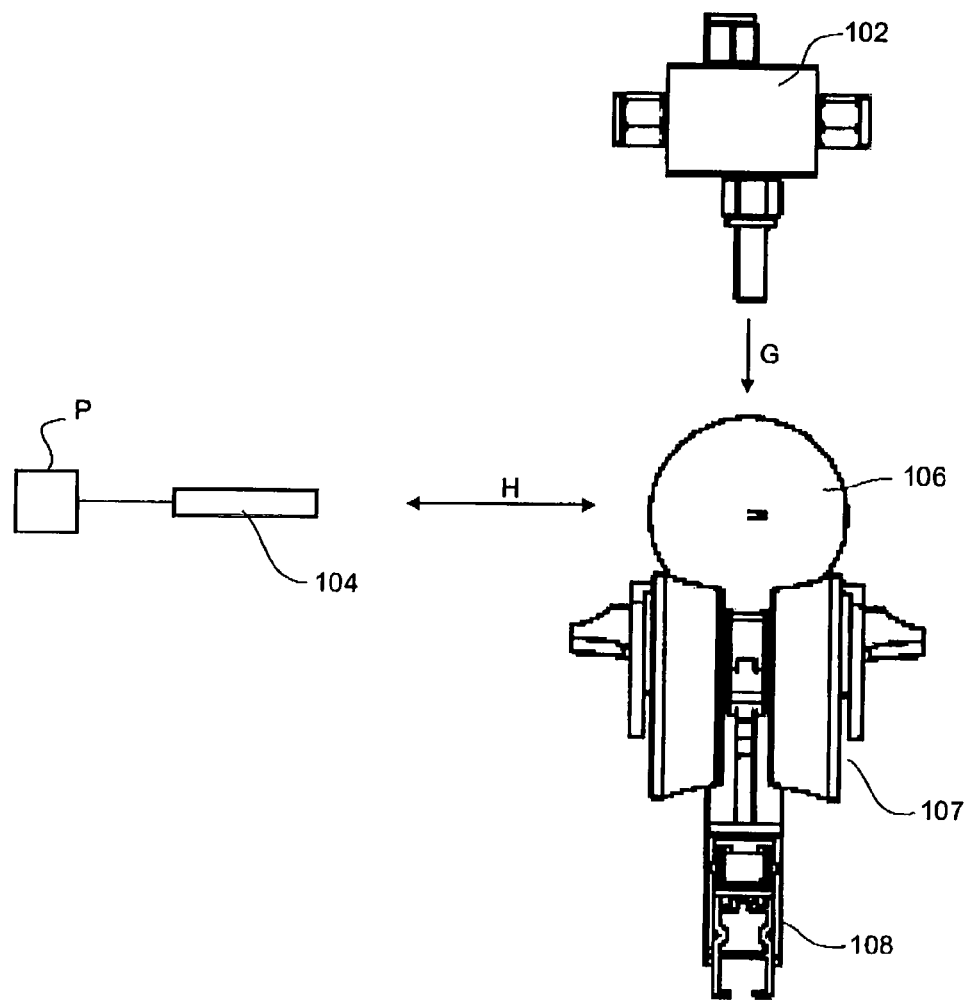
FIG. 4 shows a view of the system according to an alternative embodiment of the present invention.

The inducing arrangement 102 is horizontally spaced from the object 106 being measured, such that the impulse of fluid from the inducing arrangement impinges a side surface of the object 106 along a path G, as shown in FIGS. 1-3. Alternatively, referring to FIG. 4, the inducing arrangement 102 is vertically spaced from the object 106 being measured such that the impulse of fluid from the inducing arrangement 102 impinges a top surface of the object 106 in a holder 107 that is conveyed on a conveyor 108. In the embodiment shown in FIG. 4, the detector 106 is coupled to a processor P and is horizontally spaced from the object 106. In either arrangement, the inducing arrangement 102 is spaced by about 50 mm to about 200 mm from the object 106 being measured.

An example of a first embodiment valve 300 of the present invention of the inducing arrangement in operation is shown in FIGS. 5 to 9B. The valve 300 comprises a housing 302 having a bore 304, an inlet port 306, and an outlet port 308 substantially close to the inlet port 306. The valve 300 further comprises a reciprocable spool valve member 301 moveable within the bore 304.

Fluid from a fluid source such as a source of pressurised gas can be delivered into the bore 304 though the inlet port 306 and fluid from within the bore 306 can be delivered through the outlet port 308. The inlet port 306 and the outlet port 308 are positioned to be substantially opposite from one another. According to FIG. 5, the inlet port 306 and the outlet port 308 are directly opposite one another.

The valve 300 generates an impulse of fluid between about 0.2 MPa and about 3.0 MPa.

The output port 308 of the valve 300 may have a nozzle 310 fitted, for example a 50 mm tube.

Figures 5, 6, 7:
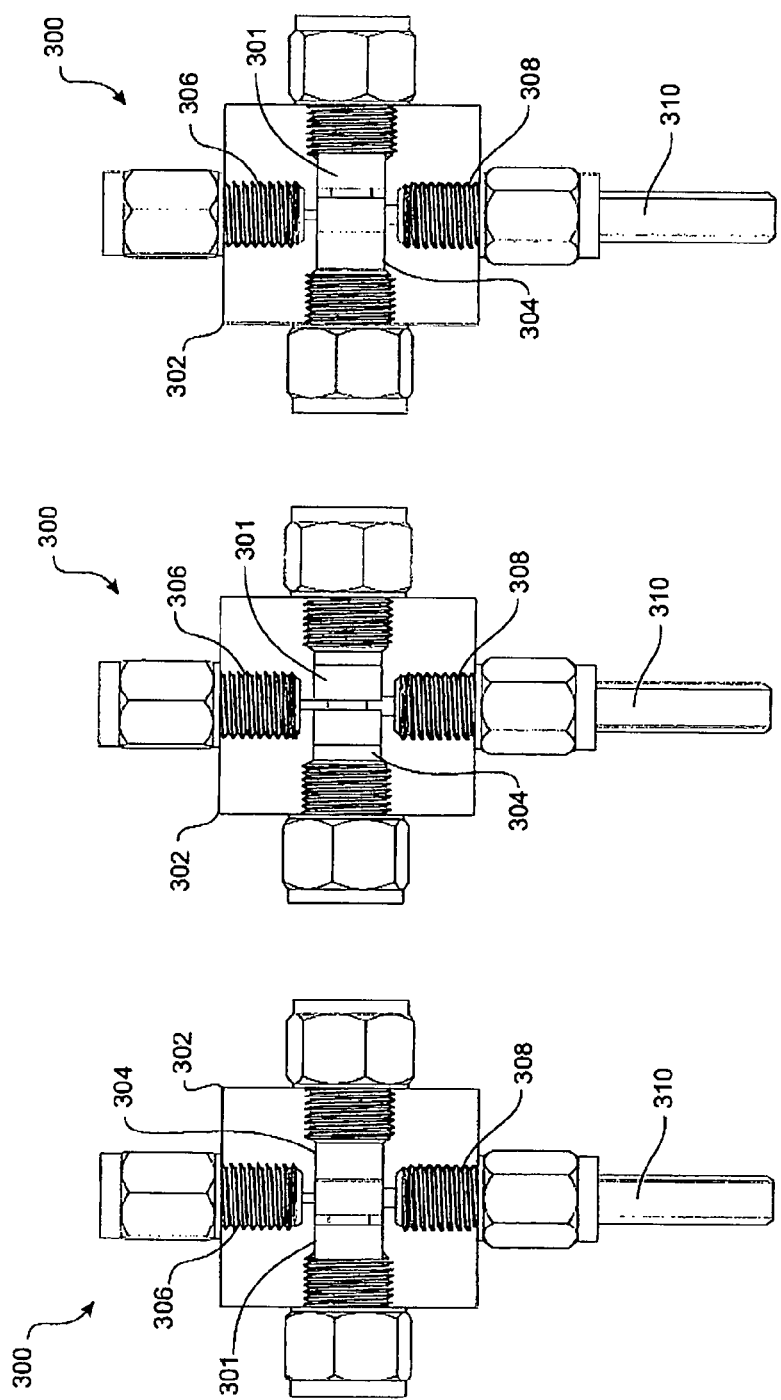
FIG. 5 shows a front sectional view of the inducing arrangement of an embodiment of the present invention, when the spool valve member is in the first substantially closed configuration.
FIG. 6 shows a front sectional view of the inducing arrangement shown in FIG. 5 when the spool valve member is in the open configuration.
FIG. 7 shows a front sectional view of the inducing arrangement shown in FIG. 5 when the spool valve member is in the second substantially closed configuration.
Figure 8A:
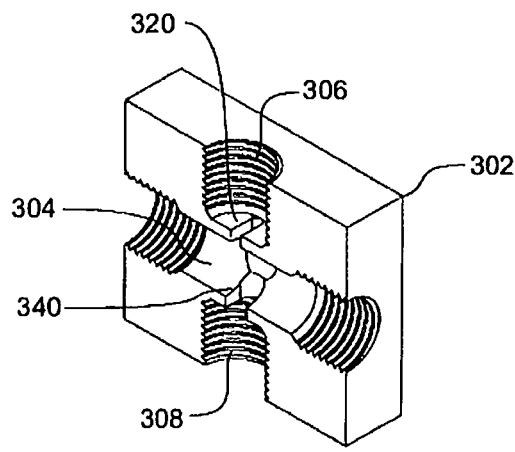
FIG. 8A shows a sectional perspective view of the housing of the inducing arrangement of FIG. 5.
Figure 8B:
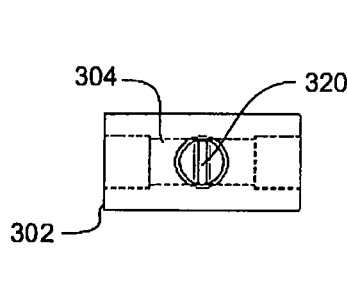
FIG. 8B shows a top view of the housing of the inducing arrangement of FIG. 5.
Figure 8C:
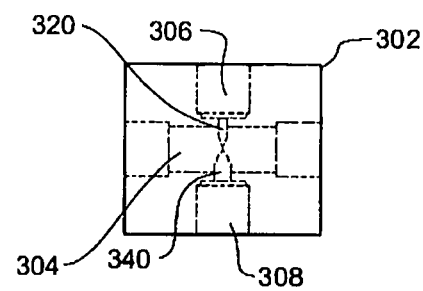
FIG. 8C shows a front view of the housing of the inducing arrangement of FIG. 5.
Figure 8D:
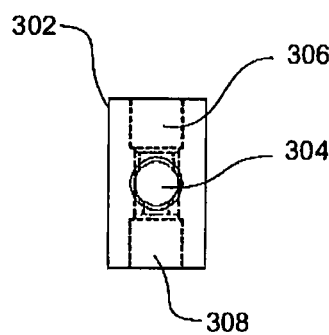
FIG. 8D shows a side view of the housing of the inducing arrangement of FIG. 5.
Figure 8E:
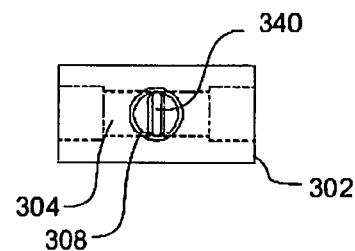
FIG. 8E shows a bottom view of the housing of the inducing arrangement of FIG. 5.

Referring still to FIGS. 5 to 7, the spool valve member 301 is moveable within the bore 304 of the housing 302 between a first substantially closed configuration (FIG. 5), an open configuration (FIG. 6), and a second substantially closed configuration (FIG. 7). The spool valve member 301 is moveable from one of the substantially closed configurations to the open configuration to the other substantially closed configurations in a single linear stroke of the spool valve member 301 within the bore 304. A single stroke of the spool valve member 301 corresponds to the movement of the spool valve member 301 within the bore 304 in a single linear/transverse direction from one end of the bore to the other end of the bore 304 which causes the spool valve member 301 to progress from one of the substantially closed configurations to the open configuration to the other substantially closed configuration. The valve member 301 moves in a direction orthogonal to the axes of the inlet port 306 and outlet port 308.

In a single stroke, the spool valve member 301 is in the open configuration for a brief period (of the order of milliseconds) and the resulting pulse of air impacts on the object, causing the object to physically vibrate. The single stroke of the spool valve member 301 within the bore 304 takes about 30 milliseconds to about 70 milliseconds. In particular, the single stroke of the spool valve member 301 takes about 50 milliseconds, and an impulse of fluid is generated by the valve 300 every 50 milliseconds. Compared to existing inducing arrangements with a spool valve, the valve 300 of the present invention has a long cycle time but a brief open time in which the spool valve member 301 is in the open configuration.

The inducing arrangement comprises a driving arrangement (not shown in the drawings) for moving the spool valve member 301 within the bore 304. In a preferred embodiment, the spool valve member 301 is pneumatically driven and the driving arrangement is a pneumatic valve connected to at least one end of the bore 304. The pneumatic valve 300 is operated accordingly to drive the spool valve member 301 from one substantially closed configuration to the other substantially closed configuration and back. In particular, the spool valve member 301 is driven by moderate-pressure air provided at either of two secondary ports, each port located at either end of the bore 304. The moderate-pressure air would typically be provided by a conventional five-port pneumatic valve, not necessarily a fast-acting one. High-pressure air form the inlet port 306 can pass to the outlet port 308 and nozzle ('barrel') 310 only for the brief period that the slots are adjacent when the spool valve member 301 is in the open configuration.

Preferably, the valve 300 is arranged to generate an impulse of fluid though the outlet port in a single stroke of the spool valve member 301 in the bore 304. The impulse has a duration corresponding to an amount of time the spool valve member 301 remains in the open configuration during the stroke. Preferably, the impulse has a substantially short duration. Preferably, the duration of the impulse is less than about 5 milliseconds. Preferably, the duration of the impulse is less than about 3 milliseconds. Preferably, the duration of the impulse is about 1 millisecond.

FIGS. 8A to 8E show views of the housing 302 of the valve 300. The housing 302 has a width of about 22 mm, a length of about 44 mm and a height of about 38 mm. The inlet port 306 and outlet port 308 are respectively substantially transverse to the bore 304. The bore 304 is substantially cylindrical, with a diameter of about 10 mm and a length that extends through the length of the housing 302. The inlet port 306 and outlet port 308 are also substantially cylindrical. The inlet port 306 has an entry aperture 320 leading into the bore 304. The outlet port 308 has an exit aperture 340 which also leads into the bore 304. The entry aperture 320 and exit aperture 340 are substantially the narrowest parts of the inlet port 306 and outlet port 308 respectively. The entry aperture 320 is substantially narrower than the exit aperture 340. The entry aperture 320 is a slot having a width of 2 mm and a length of 10 mm. The entry aperture 340 is a slot having a width of 4 mm and a length of 10 mm. The entry aperture 320 and exit aperture 340 are substantially opposite each other and are separated from each other by a distance of about 14 mm.

Figure 9A:
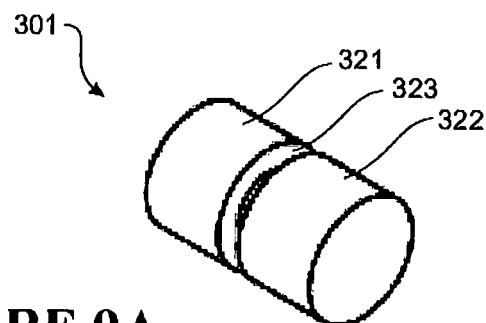
FIG. 9A shows a perspective view of the spool valve member of the inducing arrangement of FIG. 5.
Figure 9B:
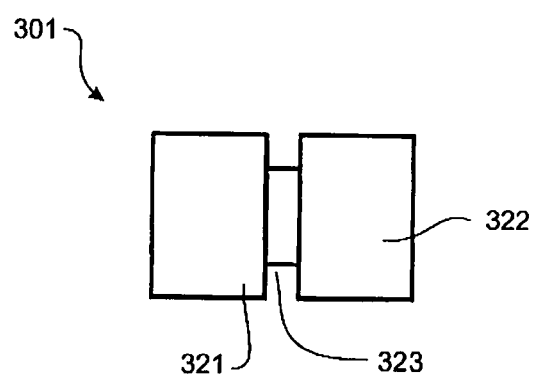
FIG. 9B shows a front view of the spool valve member of the inducing arrangement of FIG. 5.
Figure 13A:
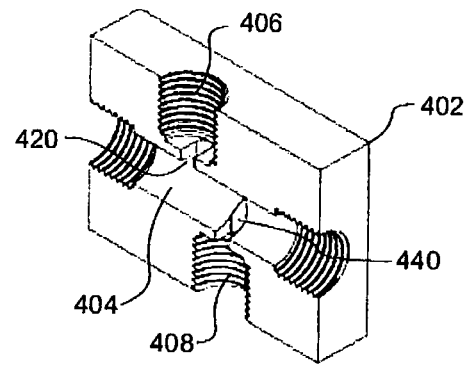
FIG. 13A shows a sectional perspective view of the housing of the inducing arrangement of FIG. 10.
Figure 13B:
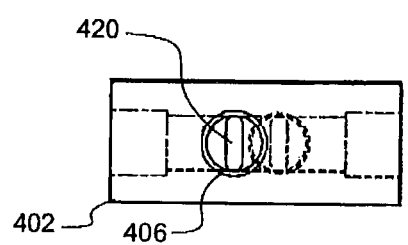
FIG. 13B shows a top view of the housing of the inducing arrangement of FIG. 10.
Figure 13C:
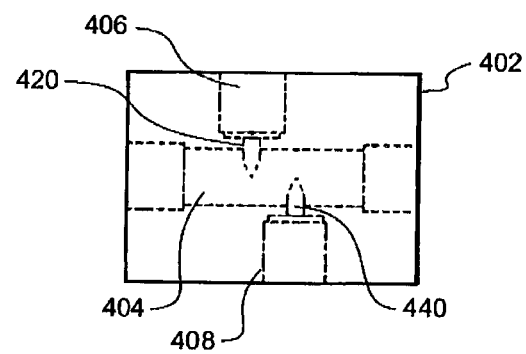
FIG. 13C shows a front view of the housing of the inducing arrangement of FIG. 10.
Figure 13D:
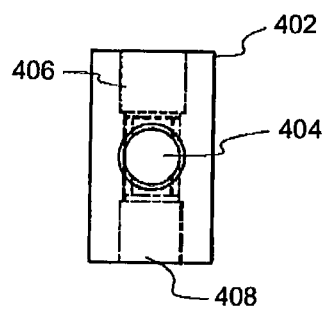
FIG. 13D shows a side view of the housing of the inducing arrangement of FIG. 10.
Figure 13E:
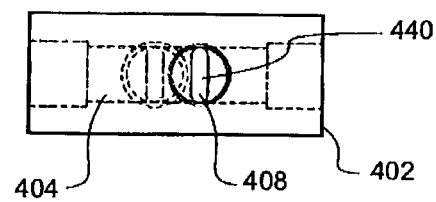
FIG. 13E shows a bottom view of the housing of the inducing arrangement of FIG. 10.

Referring to FIGS. 9A and 9B, the spool valve member 301 has two restricting sections 321, 322. Each restricting section 321, 322 is dimensioned to substantially restrict fluid flow from the inlet port 306 to the outlet port 308 when the spool valve member 301 is in either of the substantially closed configurations. The restricting sections 321,322 are substantially cylindrical, each having a diameter of about 10 mm and a length of about 7 mm. A moderate leakage of air when the spool valve member 301 is nominally closed in the substantially closed configurations will be acceptable, because it does not significantly interfere with the impact on the object when the valve opens. Acceptance of leakage means that tolerances in the valve components will not need to be as tight as they would be in conventional pneumatic valves, and therefore manufacturing costs will be lower.

The spool valve member 301 has a delivery section 323 located in between the two restricting sections 321, 322. The delivery section 323 is dimensioned to substantially allow fluid flow from the inlet port 306 to the outlet port 308 when the spool valve member 301 is in the open configuration. In the embodiment shown in FIGS. 9A and 9B, the delivery section 323 is substantially cylindrical with a diameter of about 6 mm and a length of about 2 mm. The delivery section 323 could be a narrow slot positioned between the two restricting sections 321, 322. The delivery section 323 has a width substantially equal to the width of the entry aperture 320 of the inlet port.

In an alternative embodiment of this valve 300 or the valves 400, 500 described below, the spool valve member may prevent fluid flow from the inlet port to the outlet port through the spool valve member when the spool valve member is in either of the substantially closed configurations.

FIGS. 10 to 12 show the operation of a second embodiment valve 400 of the inducing arrangement of the system of the present invention. Unless described below, the features and operation of the valve 400 are generally the same as described above for valve 300, and like reference numerals indicate like parts with the addition of 100. The second embodiment valve 400 has a similarly-driven spool valve member 401 (with a wider delivery section than the previous spool valve member) travelling past an offset inlet port 406 and outlet port 408 (which are not necessarily narrow). FIG. 11 shows the spool valve member in the open configuration, while FIGS. 10 and 12 show the spool valve member in the substantially closed configurations. Similar to the previous valve 300, flow from the inlet port 406 to the outlet port 408 will occur only for a short time when the spool valve member 401 is in the open configuration.

The spool valve member 401 of the second embodiment valve 400 may be easier to manufacture compared to the spool valve 301 of the first embodiment valve 300. The spool valve member 401 of the alternative valve 400 has a wider slot compared to the slot of the valve member 301. It is much easier to create the wider slot using conventional machining tools. Additionally, a wider slot is less susceptible to blockage.

FIGS. 13A to 13E show views of the housing 402 of the valve 400. The housing 402 has a width of about 22 mm, a length of about 52 mm and a height of about 38 mm. The inlet port 406 and outlet port 408 are respectively substantially transverse to the bore 404. The bore 404 is substantially cylindrical with a diameter of about 10 mm and a length that extends through the length of the housing 402. The inlet port 406 and outlet port 408 are also substantially cylindrical. The inlet port 406 has an entry aperture 420 leading into the bore 404. The outlet port 408 has an exit aperture 440 which also leads into the bore 404. The entry aperture 420 and exit aperture 440 are substantially the narrowest parts of the inlet port 406 and outlet port 408 respectively. The entry aperture 420 is substantially narrower than the exit aperture 440. The entry aperture 420 is a slot having a width of 2 mm and a length of about 10 mm. The entry aperture 340 is a slot having a width of 3 mm and a length of 10 mm. The entry aperture 420 and exit aperture 440 are separated from each other by a height of about 14 mm, and their axes are separated by a distance of about 8 mm.

Figure 14A:
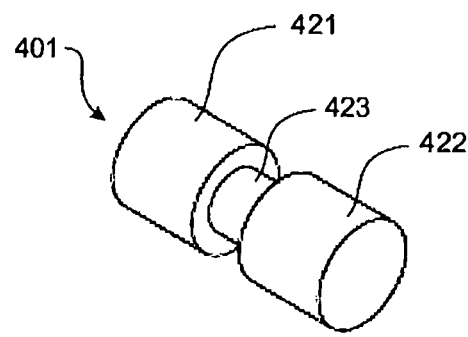
FIG. 14A shows a perspective view of the spool valve member of the inducing arrangement of FIG. 10.
Figure 14B:
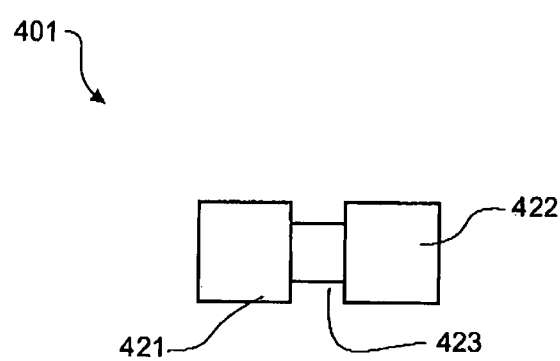
FIG. 14B shows a front view of the spool valve member of the inducing arrangement of FIG. 10.
Figure 18:
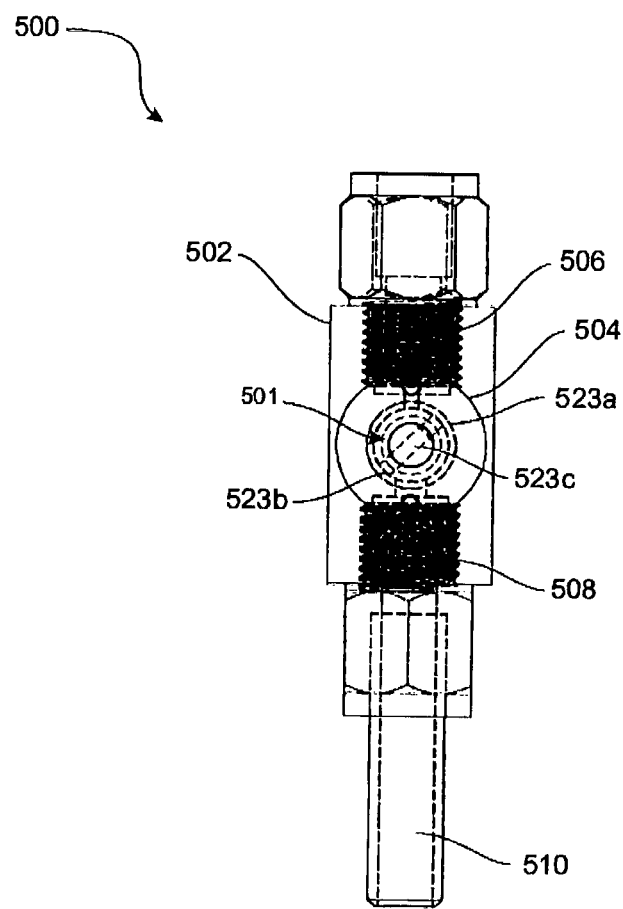
FIG. 18 is a side view of the inducing arrangement shown in FIG. 15 when the spool valve member is in one of the substantially closed configurations.

Referring to FIGS. 14A and 14B, the spool valve member 401 has two restricting sections 421, 422. Each restricting section 421, 422 is dimensioned to substantially restrict fluid flow from the inlet port 406 to the outlet port 408 when the spool valve member 401 is in either of the substantially closed configurations. The restricting sections 421 and 422 are substantially cylindrical, each having a diameter of about 10 mm and a length of about 9.25 mm. Similar to the embodiment shown in FIGS. 9A and 9B, a moderate leakage of air when the spool valve member 401 is nominally closed in the substantially closed configurations will be acceptable, because it does not significantly interfere with the impact on the object when the valve opens. Acceptance of leakage means that tolerances in the valve components will not need to be as tight as they would be in conventional pneumatic valves, and therefore manufacturing costs will be lower.

The spool valve member 401 has a delivery section 423 located in between the two restricting sections 421, 422. The delivery section 423 is dimensioned to substantially allow fluid flow from the inlet port 406 to the outlet port 408 when the spool valve member 401 is in the open configuration. In the embodiment shown in FIGS. 14A and 14B, the delivery section 423 is cylindrical with a diameter of about 6 mm and a length of about 5.5 mm. The delivery section 423 could be a narrow slot positioned between the two restricting sections 421, 422.

FIGS. 15 to 18 show the operation of a third embodiment valve 500 of the inducing arrangement of the present invention. Unless described below, the features and operation of the inducing arrangement are the same as described above for valve 300, and like reference numerals indicate like parts with the addition of 200. In this embodiment, rather than being a linearly reciprocable spool valve, the spool valve member 501 is rotatable within the bore 504 of the housing 502. The rotation axis of the spool valve member 501 is orthogonal to the axes of inlet and outlet ports 506, 508.

The spool valve member 501 comprises a hollow cylindrical section 501a having opposed slots 523a, 523b in the outer wall of the cylindrical section. A through channel 523c shown in FIG. 18 couples the two slots 523a, 523b. The hollow cylindrical section 501a is positioned between two intermediate reduced diameter portions 501b, 501c, which rotatably mount the spool valve member 501 in bearings 507 of the housing 502. A shaft 501d projects from one of the bearings, to enable the rotatable spool valve member 501 to be rotatably driven by a suitable means such as a motor or a solenoid for example.

When the rotatable spool valve member 501 is in the open configuration shown in FIG. 15, fluid may flow from the inlet port 506, to the outlet port 508. When the spool valve member 501 is in one of the substantially closed configuration shown in FIGS. 16 and 17, fluid flow from the inlet port 506 to the outlet port 508 is substantially restricted. As with valves 300 and 400, a moderate leakage of air when the spool valve member 501 is in a substantially closed configuration will be acceptable, because it does not significantly interfere with the impact on the object when the valve opens.

Again, as with the embodiments 300, 400 described above, the spool valve member 501 is movable within the bore of the housing 502 between a first substantially closed configuration (eg FIG. 16), an open configuration (FIG. 15), and a second substantially closed configuration (eg FIG. 17) in a single direction of motion of the spool valve member 501 within the bore 504. In this embodiment, that movement can occur within a single rotation of the rotatable spool valve member 501 in a single direction.

The valve 500 is preferably configured to provide an impulse of fluid through the outlet port 508 of less than about 5 milliseconds, and preferably less than about 3 milliseconds. Preferably, the duration of the impulse is about 1 millisecond. As there are opposed opening slots 523a, 523b, the delay between impulses for a given speed of movement of the spool valve member 501 may be faster than that described for the valves 300, 400 above. Within a single rotation of the spool valve member 501, the spool valve member 501 can move from a first substantially closed configuration, through a first substantially open configuration, through a second substantially closed configuration, to a second substantially open configuration.

The valves 300, 400, 500 described above are to produce a pulse length of only a millisecond or so even with large air volumes. They do not involve a slow acceleration of the valve mechanism to start the air flow: the spool valve members are already accelerated to an adequate speed, and in a preferred embodiment to near full speed, when fluid communication between the inlet port and outlet port is enabled, and is still travelling at full speed when the fluid communication is substantially disabled again. Unlike conventional fast valves which involve fast control of the source to produce an pulse of a desired width, the valves of the present invention generate a short pulse by having the source operating at an adequate speed and by having a valve member movable relative to the source and outlet which disrupts or briefly enables the flow of fluid from the source to the outlet accordingly to produce a pulse of a desired width depending on the speed and the width of the slot of the valve member. Where dimensions of the inducing arrangement have been provided, those dimensions are merely examples of dimensions that may be suitable for the inducing arrangement, and other dimensions are also possible.

The resulting vibrations can then be detected using a detector 104, such as a laser Doppler vibrometer (LDV) focussed on the object.

The Detector

Referring to FIGS. 1 to 3, the detector 104 remotely detects the physical vibration of the object 106. The detector 104 does not contact the object 106 when detecting the physical vibration of the object 106.

According to an embodiment of the present invention, the detector 104 is a Laser Doppler Vibrometer (LDV). Processing the signals from the LDV allows the frequency spectrum of the vibrations to be calculated and the resonant frequency of the object determined. By combining the resonant frequency with the object mass and shape information, the flesh stiffness (firmness) can be determined.

Configuration in a Multiple-Lane or Conveyor System

Figure 19:
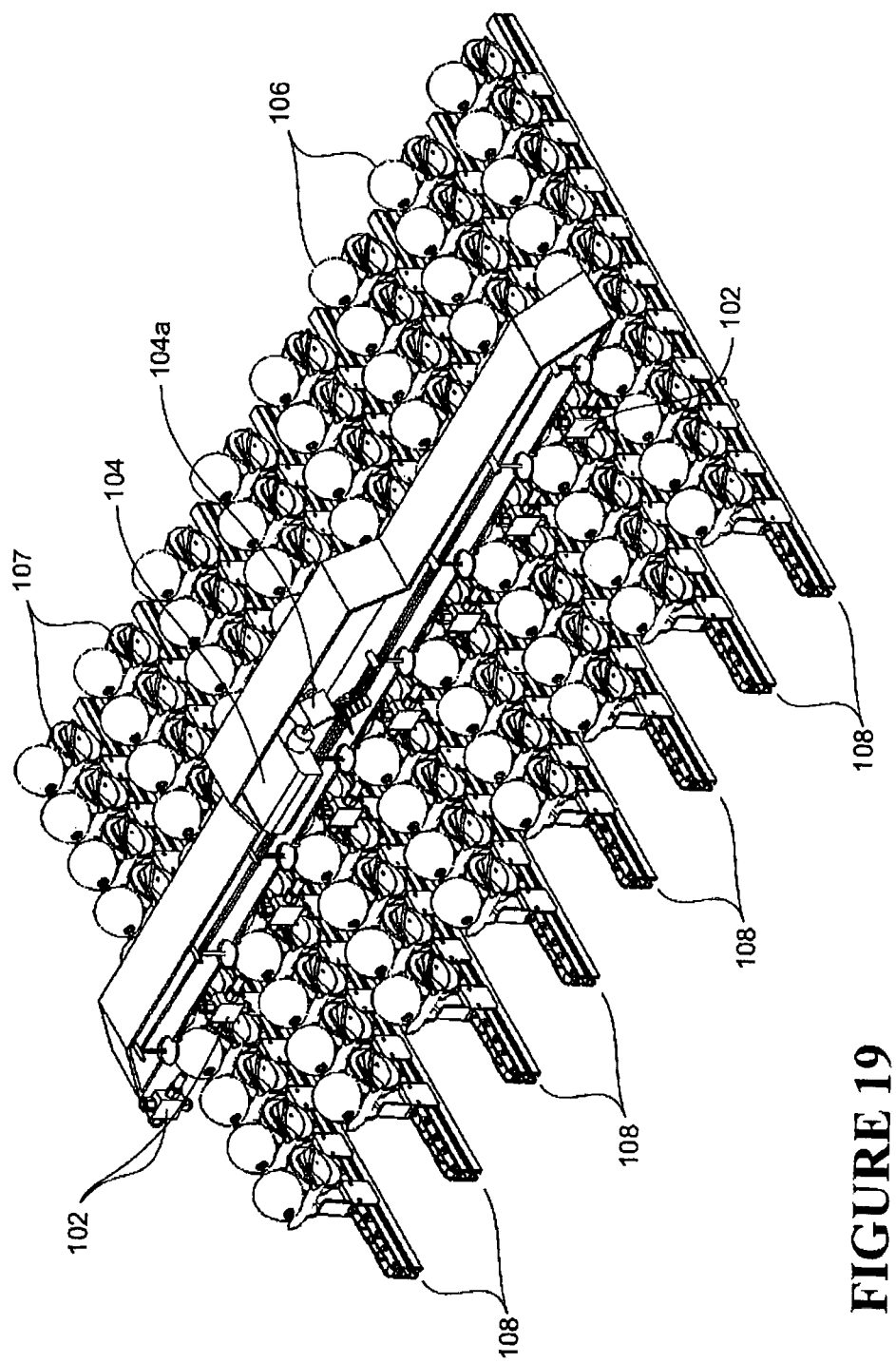
FIG. 19 shows a system of an alternative embodiment of the present invention with multiple conveying lanes.
Figure 20:
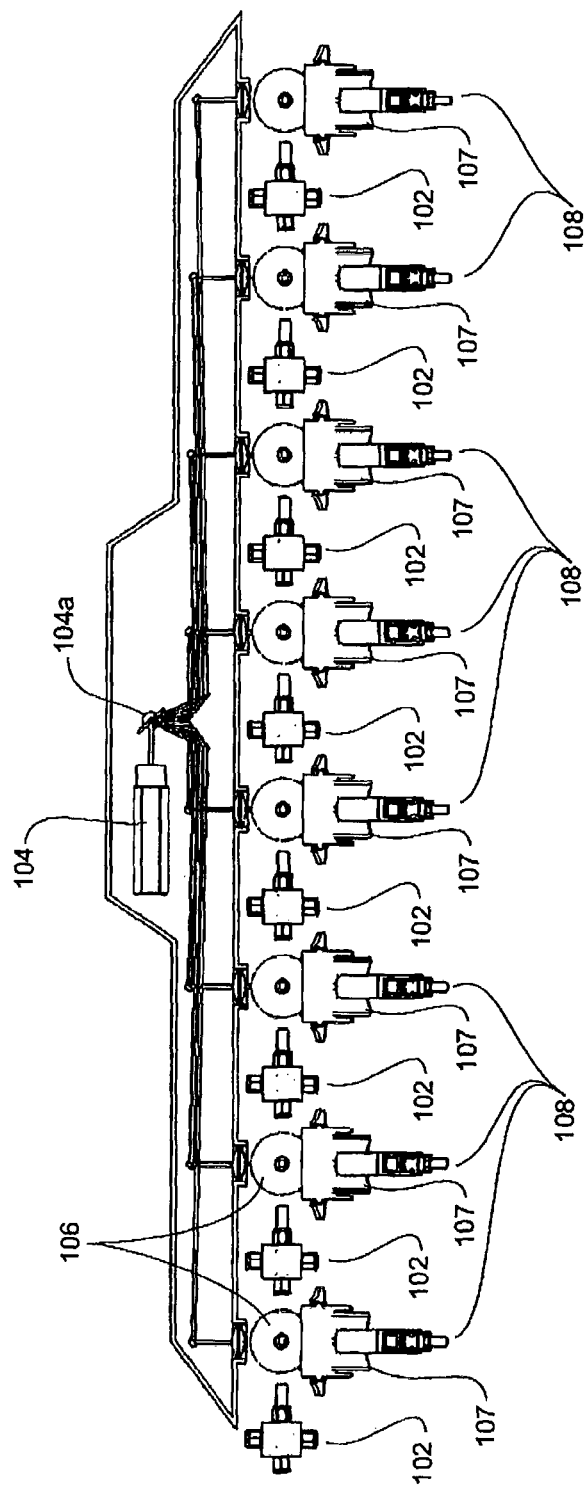
FIG. 20 shows an end view of the system of FIG. 19.

Referring to FIGS. 19 and 20, where the system is implemented in a multiple-lane or a conveyor system, the system is arranged such that signals between the detector 104 and the object 106 have a direction substantially perpendicular to a movement direction of the object 106 being conveyed. The direction of the signals between the detector 104 and the object 106 is substantially 90°±0.5° to a direction of movement of the object 106 being conveyed.

In the multiple-lane or conveyor embodiment of the present invention, the detector 104 comprises an optical guide 104a for selectively communicating signals between the detector 104 and from the object 106 in one of the holders 107 on one of a plurality of conveyors 108. Each conveyor 108 is adapted to convey a series of objects 106. In that setup, the system comprises a plurality of inducing arrangements 102. Each inducing arrangement 102 is assigned to one of the plurality of conveyors 108. According to a preferred embodiment, the optical guide 104a is an electronically-movable deflection mirror.

It will be appreciated that other embodiments of the present invention could be implemented for a different number of lanes or conveyors, such as one, two, or more lanes or conveyors, for example.

The Processor

Measurements collected from the detector 104 are communicated to a processor P (FIGS. 1 and 4) which is configured to determine the property of the object. The processor P may be any suitable computing device that is capable of executing a set of instructions that specify actions to be carried out. The term 'computing device' includes any collection of devices that individually or jointly execute a set or multiple sets of instructions to perform any one or more of the methods of determining a property of an object based on the signals received by the detector.

The processor P includes or is interfaced to a machine-readable medium on which is stored one or more sets of computer-executable instructions and/or data structures. The instructions implement one or more of the methods of determining a property of an object based on the signals received by the detector. The instructions may also reside completely or at least partially within the processor P during execution. In that case, the processor P comprises machine-readable tangible storage media.

The computer-readable medium is described in an example to be a single medium. This term includes single media or multiple medium. The term 'computer-readable medium' should also be taken to include any medium that is capable of storing, encoding or carrying a set of instructions for execution by the processor and that cause the processor P to perform the method of determining a property of an object based on the signals received by the detector. The computer-readable medium is also capable of storing, encoding or carrying data structures used by or associated with the instructions.

Where the system is implemented in a multiple-lane or conveyor system, the processor P may be in electrical communication with the optical guide 104a (shown in FIGS. 19 and 20) to selectively move the guide 104a between a plurality of positions to direct the detection signals between the detector and the object on a respective one of the lanes.

Results

The results of the Fluid Tap method using the system 100 described with reference to FIGS. 1 to 3, in which the inducing of the first embodiment arrangement 102 comprises the first embodiment valve 300 described with reference to FIGS. 5 to 9B, will now be discussed with reference to FIGS. 21 to 25B. The system 100 comprises the detector 104 and the processor P that have been described previously.

Figure 21:
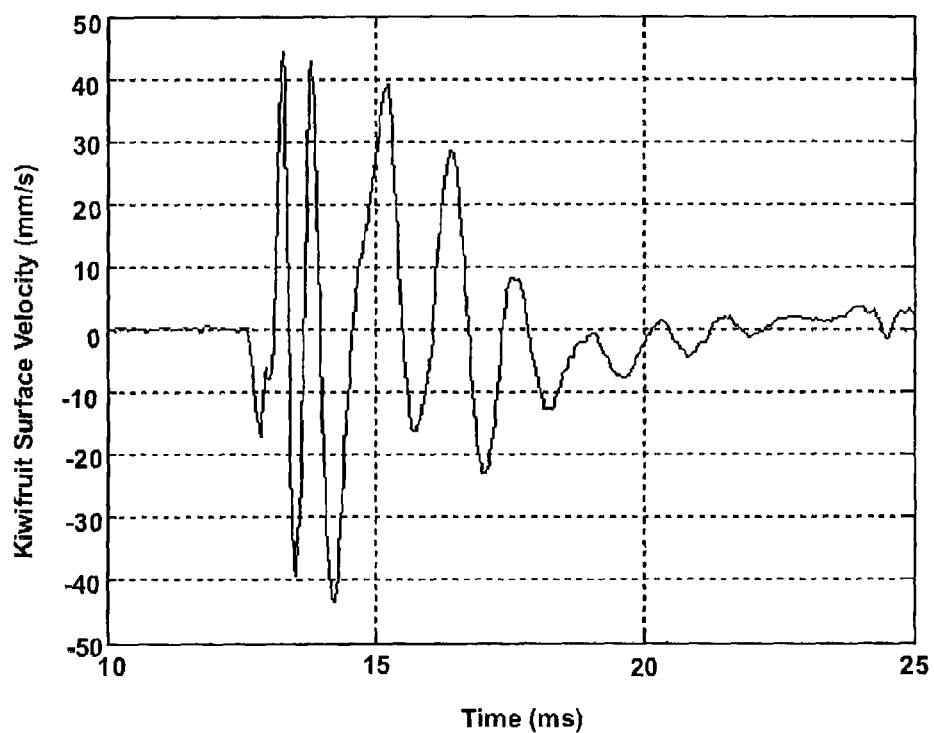
FIG. 21 shows a typical LDV recording of surface vibration of a kiwifruit impacted by an impulse of gas using a system of a first embodiment of the present invention.

FIG. 21 shows a typical LDV recording of surface vibration of a kiwifruit impacted by an impulse of gas from the valve arrangement 102 as detected by the detector 104. As seen from FIG. 21, the physical vibrations in the kiwifruit have a duration of less than about 10 milliseconds.

Figure 22:
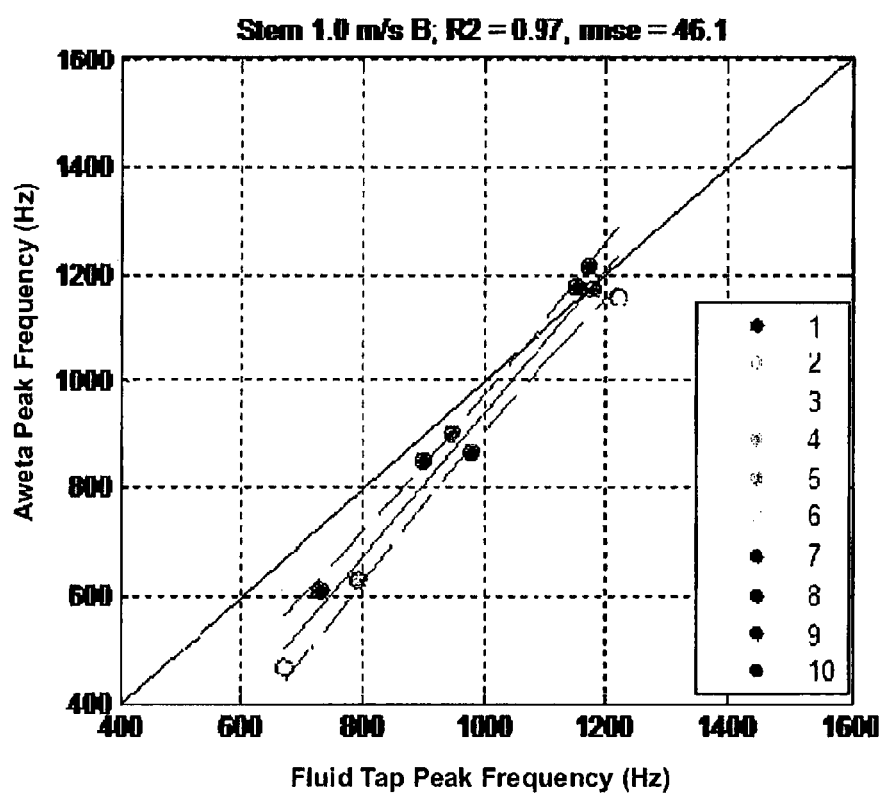
FIG. 22 shows the Peak Frequency relationships between Aweta measurements and measurements using the system of the first embodiment of the present invention for ten apples.

FIG. 22 shows the peak frequency relationships between measurements obtained from the Aweta system and measurements from the Fluid Tap system for ten apples. The Aweta measurements were taken using standard laboratory methods on static fruit. The Fluid Tap measurements were taken using the Fluid Tap method of the present invention, and stem end LDV measurement, with the fruit travelling on the conveyor at 1 meter per second. According to this figure, there is a strong correlation between the results obtained using the Aweta method and the results obtained using the Fluid Tap method of the present invention.

Because the physical vibrations of the object can be induced and detected without physically contacting the fruit and while the objects are moving, the Fluid Tap method is suited to fast-moving fruit on a conveyor.

Compared to the system described in Prussia, the Fluid Tap method is able to obtain a whole-fruit acoustic resonance measurement and it consumes much less compressed air. The table below compares the Prussia method with the Fluid Tap method of the present invention.

In practice, the Fluid Tap method does not seem to damage fruit. Placing a hand in the gas impulse causes only a slight vibration of the hand, with no discomfort.

TABLE 1

A comparison of operating parameters, as preferred ranges, for the Prussia and Fluid Tap methods.

| Method | Air pressures (MPa) | Impact durations (milliseconds) |
|---|---|---|
| Prussia (using deformation response) | 0.03-0.4 | 3 to 20 |
| Fluid Tap (using vibration response) | 0.2-3 | <3 |

Figure 23:
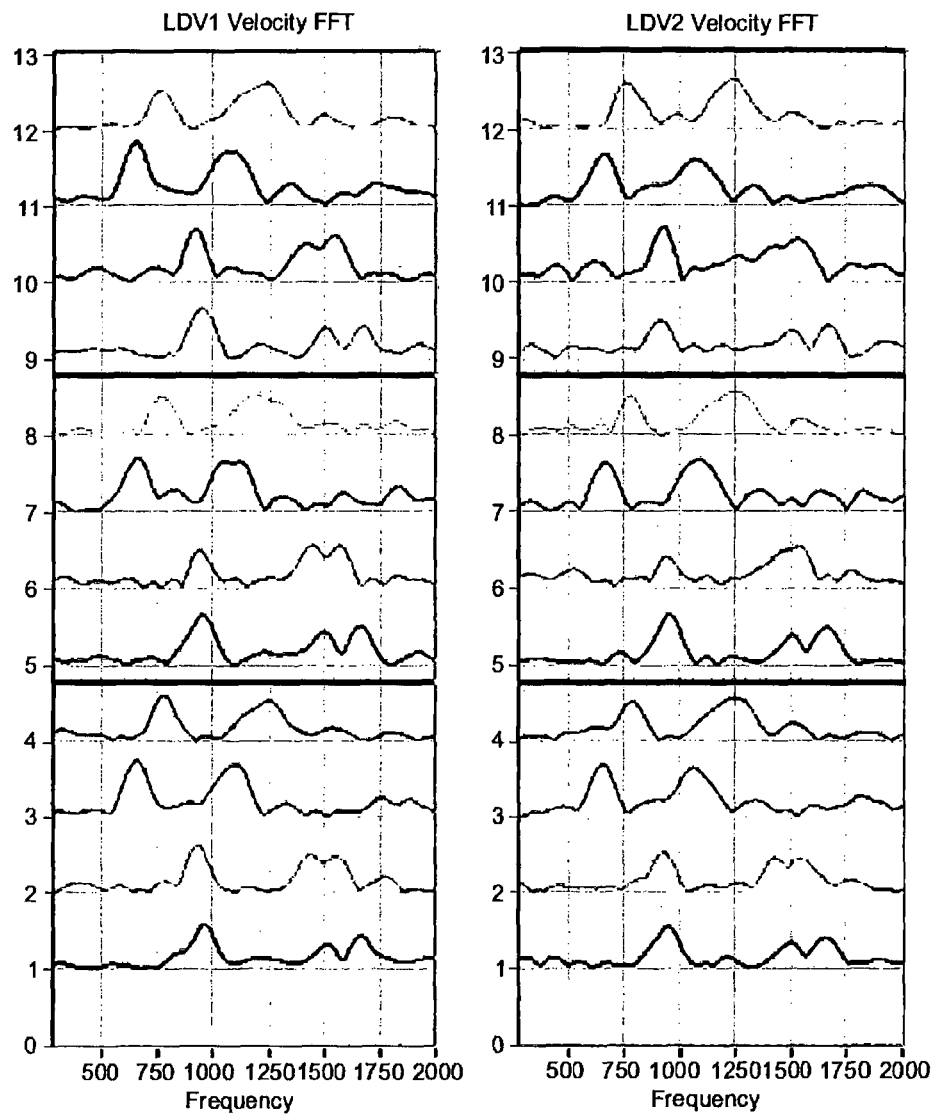
FIG. 23 comparatively shows the frequency responses obtained by two LDV detectors using the system of the first embodiment of the present invention.

FIG. 23 shows an example of measurements at varying grader speeds of 0.9, 1.2 and 1.5 meters per second (nearly 16 fruit per second). There are three sets of spectra for four apples, collected by running the four apples through the preferred embodiment system three times, each time at a different grader speed. The left and right panels are the spectra from two separate vibrometers operating at the same time, showing the consistency of measurement between instruments. The repeatability between consecutive measurements on the same apple (traces 1, 5, 9 for apple 1; traces 2, 6, 10 for apple 2; etc) is high. Traces 1-4 were recorded with a grader speed of 0.9 meters per second; traces 5-8 at 1.2 meters per second; traces 9-12 at 1.5 meters per second. There is little change in the position or clarity of the principal spectral peaks as speed increases.

Figure 24:
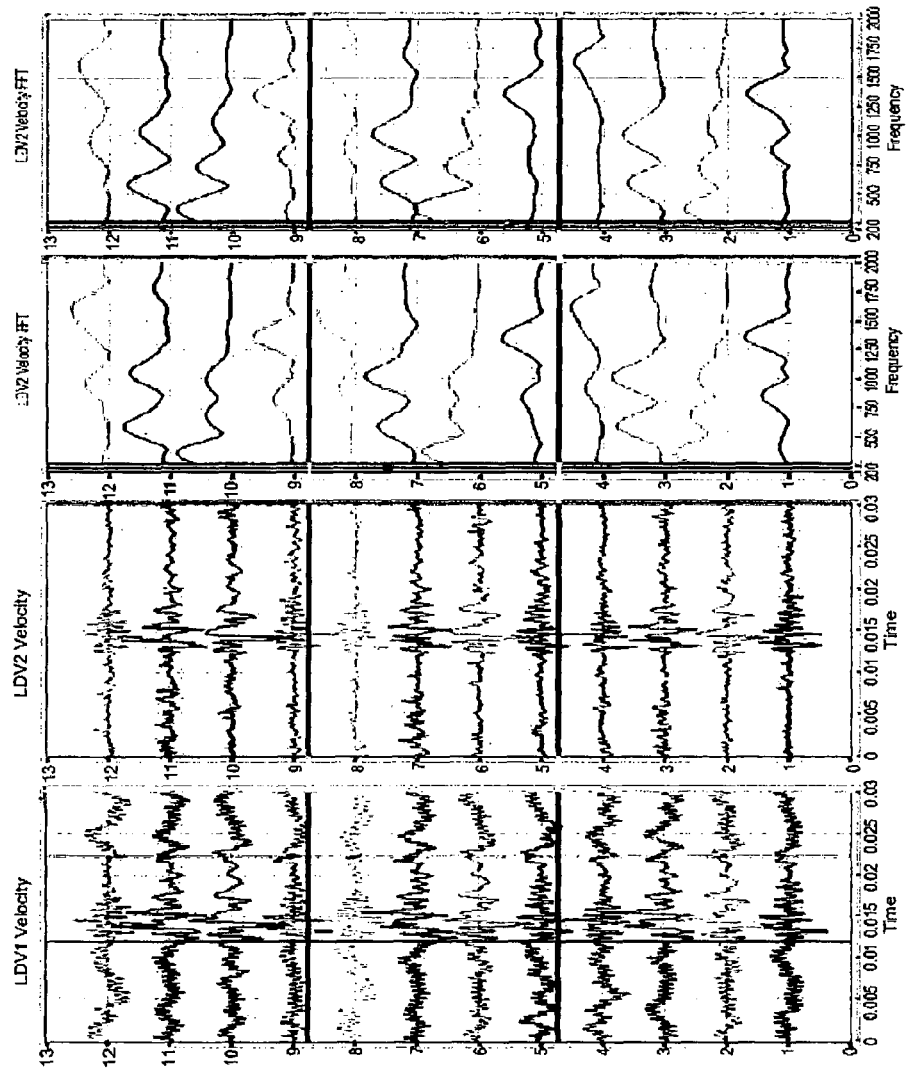
FIG. 24 shows the time and frequency responses obtained by two LDV detectors using the system of the first embodiment of the present invention.

The system 100 can achieve a signal of equal quality with only about 10 milliseconds spent per lane 108. An example of this is shown in FIG. 24. This Figure shows the time and frequency responses of two different LDVs (LDV1 and LDV2) operating at the same time on the same object. There are three sets of spectra fox four apples. Each response is collected by running the four apples through the grader three times.

The first vibrometer (LDV1) is not aimed at the grader line until the instant approximately marked by the first vertical line in the leftmost panel (at 0.012 s). Between the two vertical lines (at 0.012 s and 0.022 s), LDV1 is pointed at an apple on the grader by an electronically-movable deflection mirror. After the red line (at >0.022 s) LDV1 is again pointed away from the grader line. When it is not pointed at the grader line, LDV1 is pointed at a loudspeaker cone approximately 20 cm below the line of apples. The speaker cone is vibrated at about 1.8 kHz so that the fact that the LDV1 is pointing at a well-defined place (which could be another lane on a grader) is clearly shown by the uniform vibrations on the trace. There is an interval of about 0.002 s or less when the beam is shifting between the two targets. The signal collected for Fourier analysis and spectrum calculation is taken only from the interval between the two vertical lines at 0.012 s and 0.022 s respectively.

The second vibrometer (LDV2) was always pointed at the grader.

From the responses shown in FIG. 24, it can be seen that the responses of both detectors (LDV1 and LDV2) are substantially similar. The spectra are highly repeatable between vibrometers and for each apple. This figure illustrates that the switching of the beam from one lane to another can be achieved without significant signal degradation when the time the LDV is aimed at each lane is only about 0.01 s. Even shorter intervals can be used, with progressive broadening of the spectral peaks, giving decreased but perhaps still acceptable accuracy.

At a grader speed of 10 fruit per second (0.95 meters per second for a typical apple grader), a single vibrometer could be shared across ten lanes. The practical range of this model of vibrometer is about 2 m, and a deflected beam could reach right across a ten-lane grader.

Figure 25A:
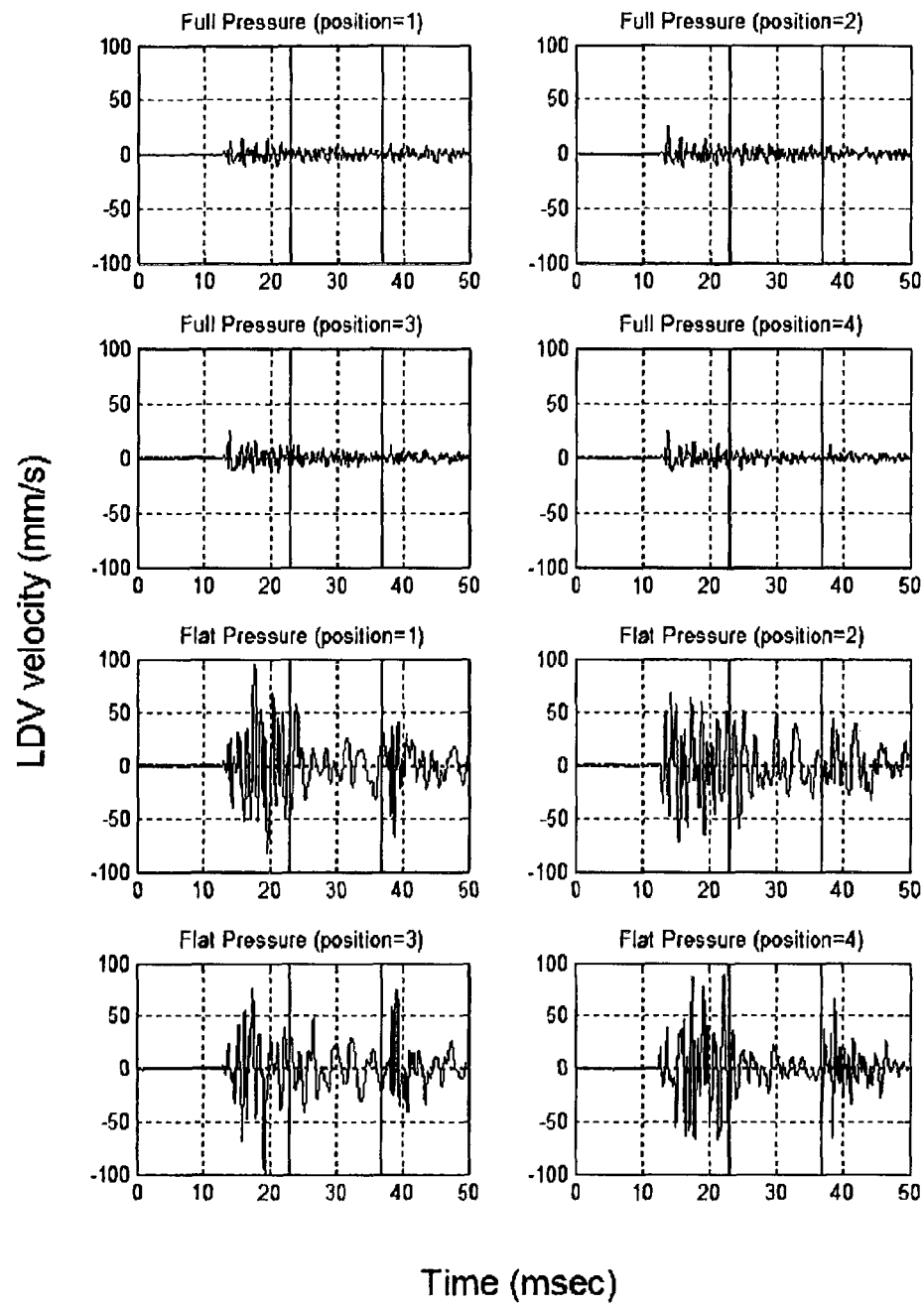
FIG. 25A shows the LDV recording for a plastic bottle using the system of the first embodiment of the present invention measured at four different positions at full pressure and measured at four different positions at reduced pressure.
Figure 25B:
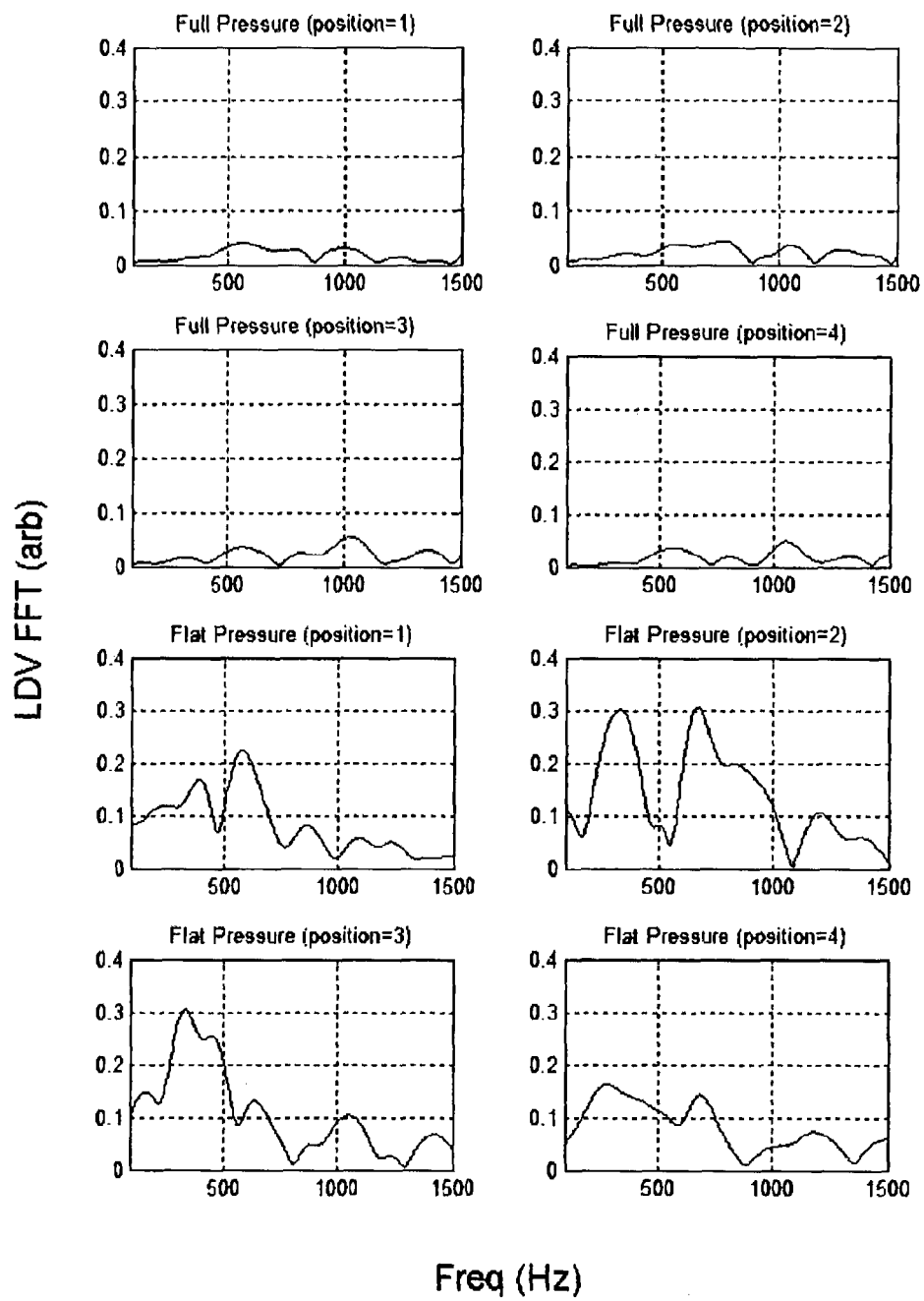
FIG. 25B shows the frequency spectra of the LDV recording in FIG. 25A.

FIG. 25A shows the LDV recording for a bottle measured at four different positions when the bottle is at full pressure and measured at four different positions when the bottle is at a reduced pressure or not pressurised, while FIG. 25B shows the frequency spectra for each LDV recording. The top four recordings and spectra are for a fully pressurised bottle while the bottom four recordings and spectra are for a bottle with a reduced pressure. The mass of the full bottles were the same. The pressure was released by decantering repeatedly (up to 10 times) between two vessels before returning the fluid to the original bottle. The amplitude of the velocity signal is substantially small for pressuried bottles, as shown in the top four plots of FIG. 25A. The velocity signal is larger for bottles with reduced pressure as shown in the bottom four plots of FIG. 25A. These Figures show that the pressurised state of an object can be determined using the Fluid Tap system.

Alternative Embodiments of the System

Figure 26:
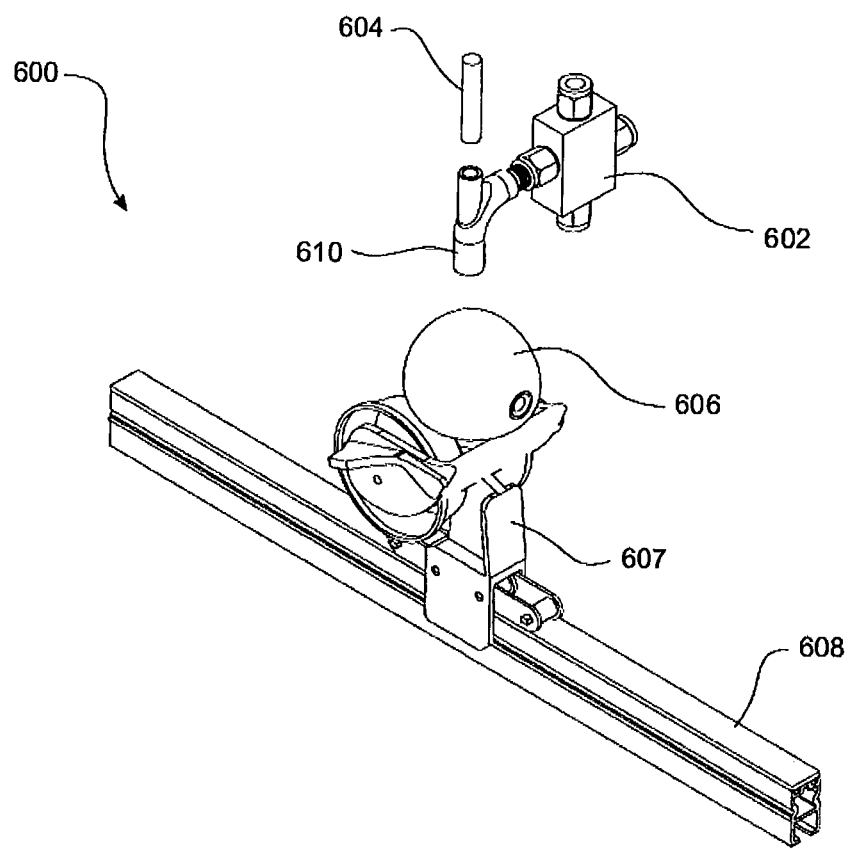
FIG. 26 shows a perspective view of the system of a second embodiment of the present invention.
Figure 27:
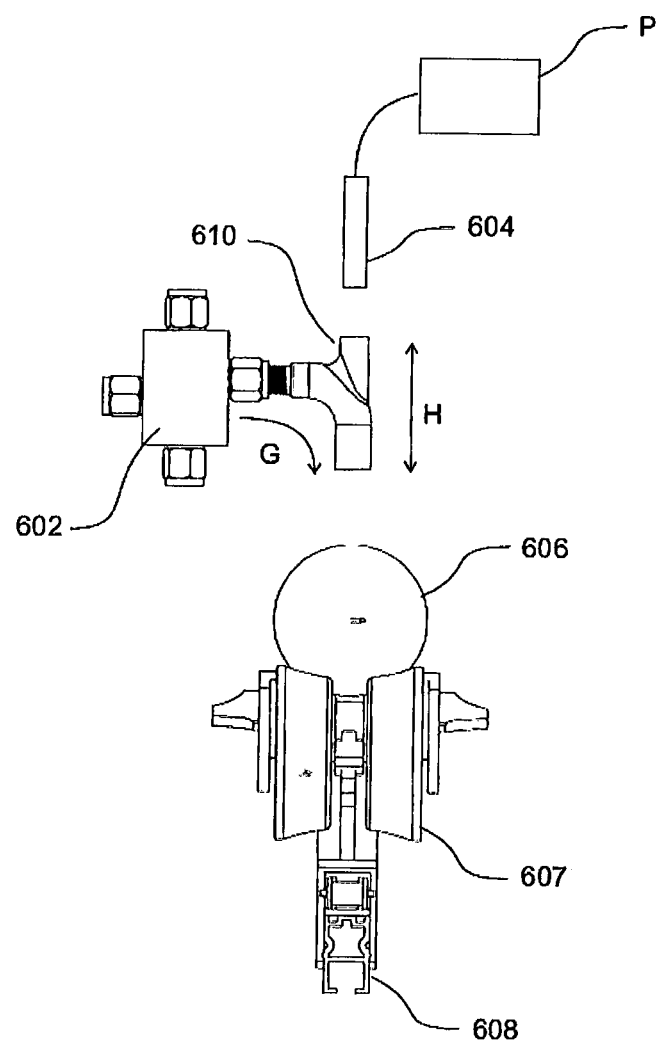
FIG. 27 shows a front view of the system shown in FIG. 26.
Figure 28:
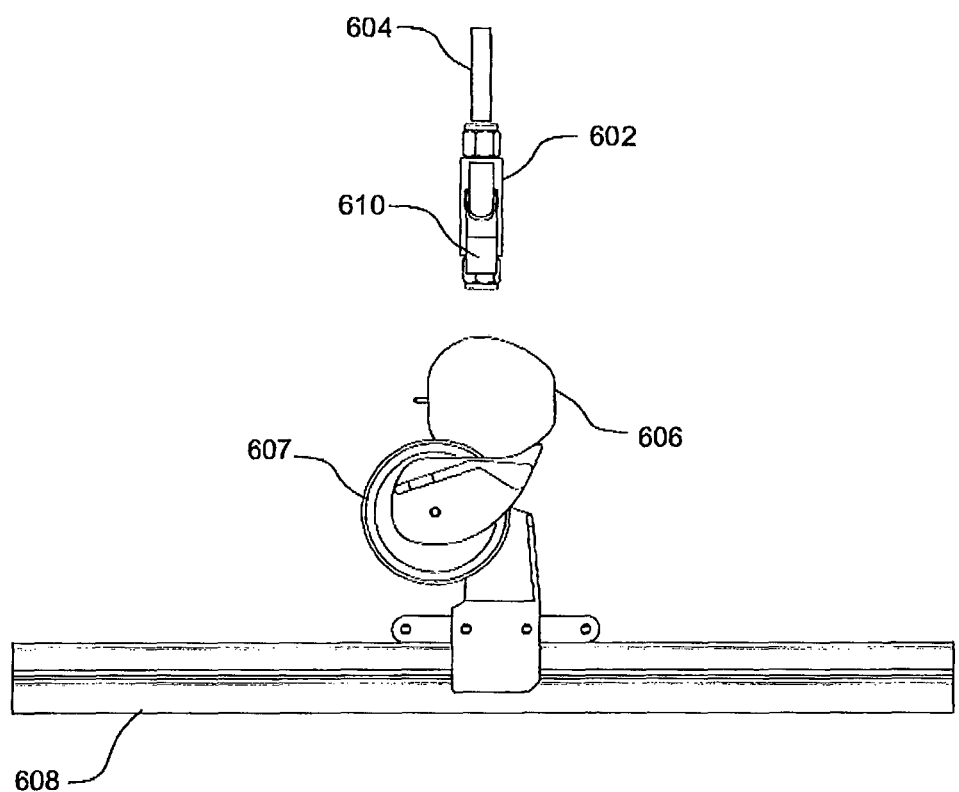
FIG. 28 shows a side view of the system shown in FIG. 26.

FIGS. 26 to 28 show a second embodiment system 600 for determining a property of an object 606. The system 600 could be used on any of the objects previously identified. Additionally, the system 600 can be configured to determine the properties previously identified. Unless described below, the features and operation of the system 600 should be considered the same as those described above, and like reference numerals indicate like parts with the addition of 500.

The system 600 generally comprises an inducing arrangement 602 and a detector 604. The inducing arrangement 602 and detector 604 may be similar to the inducing arrangements and detectors described previously. The inducing arrangement 602 may comprise any one of the first embodiment valve 300 described with reference to FIGS. 5 to 9B, the second embodiment valve 400 described with reference to FIGS. 10 to 14B, and the third embodiment valve 500 described with reference to FIGS. 15 to 18.

The system 600 further comprises an impulse guide 610 for guiding the impulse of fluid from the inducing arrangement 602 toward the object 606 in a substantially similar direction to the signals between the detector 604 and the object 606. The impulse guide 610 is preferably adapted to direct the impulse of fluid from the inducing arrangement 602 and the signals between the detector 604 and the object 606 in the same direction towards the object 606. The impulse guide 610 will be discussed in more detail below.

The system 600 further comprises a processor (shown in FIG. 27) that is coupled to the detector 604. The processor P is configured to determine the property of the object 601 based on measurements received from the detector 604. Features of the processor P have been previously described above.

The system 600 is particularly configured to determine a firmness property of an object 606 such as a fruit in a holder 607 that is conveyed down a conveyor line 608.

Similar to the previous embodiment shown in FIGS. 1 to 3, the system 600 can determine the firmness of the object 606 by impacting a short, sharp burst of fluid generated by the inducing arrangement 602 onto a location of the object 606 along a first path G and sensing (or detecting) by the detector 604 along a second path H the resulting vibrations of the object 606 by measuring the vibrations from the same location. As an additional or alternative measure, the system 600 can determine the firmness of the object 606 by impacting the impulse of fluid generated by the inducing arrangement 602 onto a location of the object 606 along the first path G and sensing (or detecting) by the detector 604 along the second path H the deformation of the object 606 at the location at which the impulse of fluid impacts. In this case, the Fluid Tap method covers the determination of a property of the object 606 based on the resulting vibrations and/or the deformation response of the object 606.

The first path G substantially converges with the second path H at least on a top surface of the object 606. The first path G is substantially non-linear, while the second path H is substantially linear. Throughout the process, the inducing arrangement 602 and the detector 604 do not physically contact the object being measured.

The Impulse Guide

Referring still to FIGS. 26 to 28, the impulse guide 610 guides the impulse of fluid towards the object in a direction of propagation that is generally coincident to a direction of signals communicated between the detector 604 and the object 606. Particularly, the impulse guide 610 is adapted to converge the path G of the impulse of fluid toward the path H of the detection signals. The direction of propagation and the direction of signals are generally coincident with each other on a top surface of the object 606.

Figure 29A:
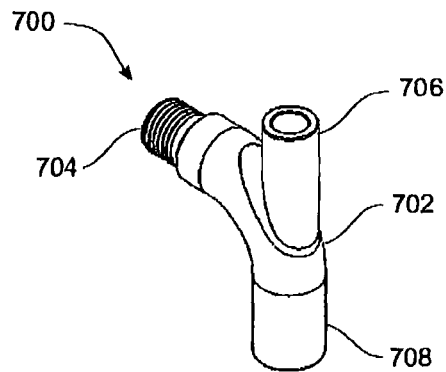
FIG. 29A shows a perspective view of an impulse guide according to a first embodiment of the invention for the system shown in FIG. 26.
Figure 29B:
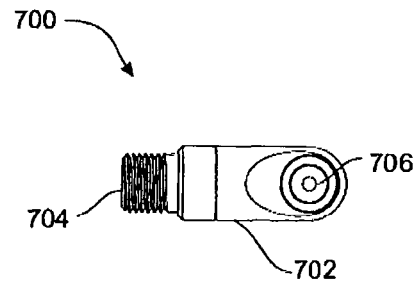
FIG. 29B shows a top view of the impulse guide shown in FIG. 29A.
Figure 29C:
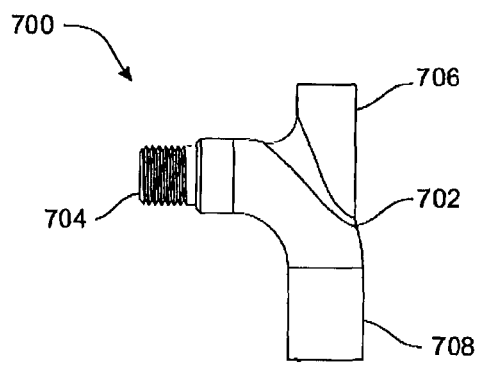
FIG. 29C shows a front view of the impulse guide shown in FIG. 29A.
Figure 29D:
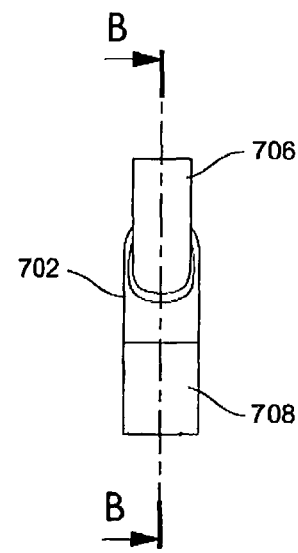
FIG. 29D shows a side view of the impulse guide shown in FIG. 29A.
Figure 29E:
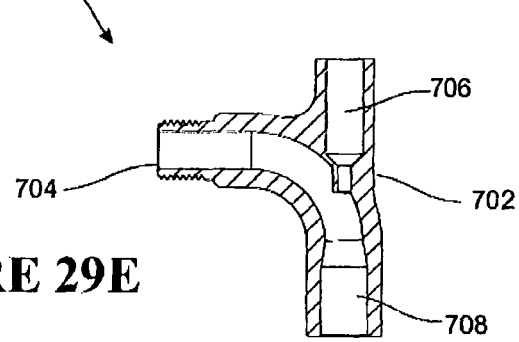
FIG. 29E shows a sectional front view of the impulse guide shown in FIG. 29A taken along the lines B-B of FIG. 29D.

FIGS. 29A to 29E show views of a first embodiment impulse guide 700. The impulse guide 700 comprises a body 702 having first arm 704 through which the impulse of fluid from the inducing arrangement is directed, a second arm 706 through which signals are communicated between the detector and the object, and a third arm 708 that is configured to be directed towards the object and is in communication with the first arm 704 and second arm 706. The third arm 708 is substantially collinear or coaxial with the second arm 706. The impulse of fluid received by the first arm 704 is configured to pass through the first arm 704 and the third arm toward the object and signals between the detector and object are configured to pass through the second arm 706 and the third arm 708. As shown in FIGS. 29B and 29E, the second arm 706 and the third arm 708 are substantially collinear or coaxial such that the signals between the detector and the object have a substantially straight path through the body 702. According to the embodiment shown in the FIGS. 29A to 29E, the first arm 702 is substantially perpendicular to the second arm 706. The path from the first arm 704 to the third arm 708 is substantially curved to allow a smooth propagation of the impulse from the inducing arrangement to the object.

FIGS. 30A to 30E show views of a second embodiment impulse guide 800. The impulse guide 800 comprises a body 802 having first arm 804 through which the impulse of fluid from the inducing arrangement is directed, a second arm 806 through which signals are communicated between the detector and the object, and a third arm 808 that is configured to be directed towards the object and is in communication with the first arm 804 and second arm 806. The third arm 808 is substantially collinear or coaxial with the second arm 806. The impulse of fluid received by the first arm 804 is configured to pass through the first arm 804 and the third arm toward the object and signals between the detector and object are configured to pass through the second arm 806 and the third arm 808. As shown in FIGS. 30B and 30E, the second arm 806 and the third arm 808 are substantially collinear such that the signals between the detector and the object have a substantially straight path through the body 802. According to the embodiment shown in the FIGS. 30A to 30E, the first arm 804 is at an angle of about 130° to the second arm 806. The path from the first arm 804 to the third arm 808 is substantially curved to allow a substantially smooth propagation of the impulse from the inducing arrangement to the object, with minimal frictional losses.

According to other embodiments, the first arm of the impulse guide may be at any angle between about 90° and less than about 180° to the third arm. According to other embodiments, the third arm is substantially collinear with the first arm, and the second arm is at any angle between about 90° and about 180° to the first arm. The impulse guide is shown to be separate from the inducing arrangement. However, according to other embodiments, the impulse guide is integral with the inducing arrangement. For example, the impulse guide may be integral with the first embodiment valve, the second embodiment valve, or the third embodiment valve.

According to other forms of the alternative embodiments of the system, an impulse guide is not present. In those embodiments, the inducing arrangement is adapted to direct an impulse of fluid to a surface of the object that is adapted to be detected by the detector. For example, the impulse of fluid from the inducing arrangement has direction of propagation towards the object that is generally coincident to a direction of signals communicated between the detector and object. The impulse of fluid and the detection signals may be generally coincident on a surface of the object, which may be a top surface of the object.

To coincide the impulse of fluid with the detection signals on a surface of the object without an impulse guide, any one of the first, second and third embodiment valves may be positioned at an appropriate angle relative to the object. Alternatively, a fourth embodiment valve may be provided, where an inlet port of the valve may be at a non-parallel angle relative to the outlet port. In that embodiment, a direction of fluid into the inlet port is at a non-parallel angle to a direction of fluid from the outlet port. The outlet port may be angled relative to the inlet port such that the direction of fluid from the outlet port is at an angle of between about 90° and about 180° from the direction of fluid into the inlet port. According to some embodiments, the outlet port is angled relative to the inlet port such that the direction of fluid from the outlet port is at an angle of about 130° from the direction of fluid into the inlet port.

Figure 31:
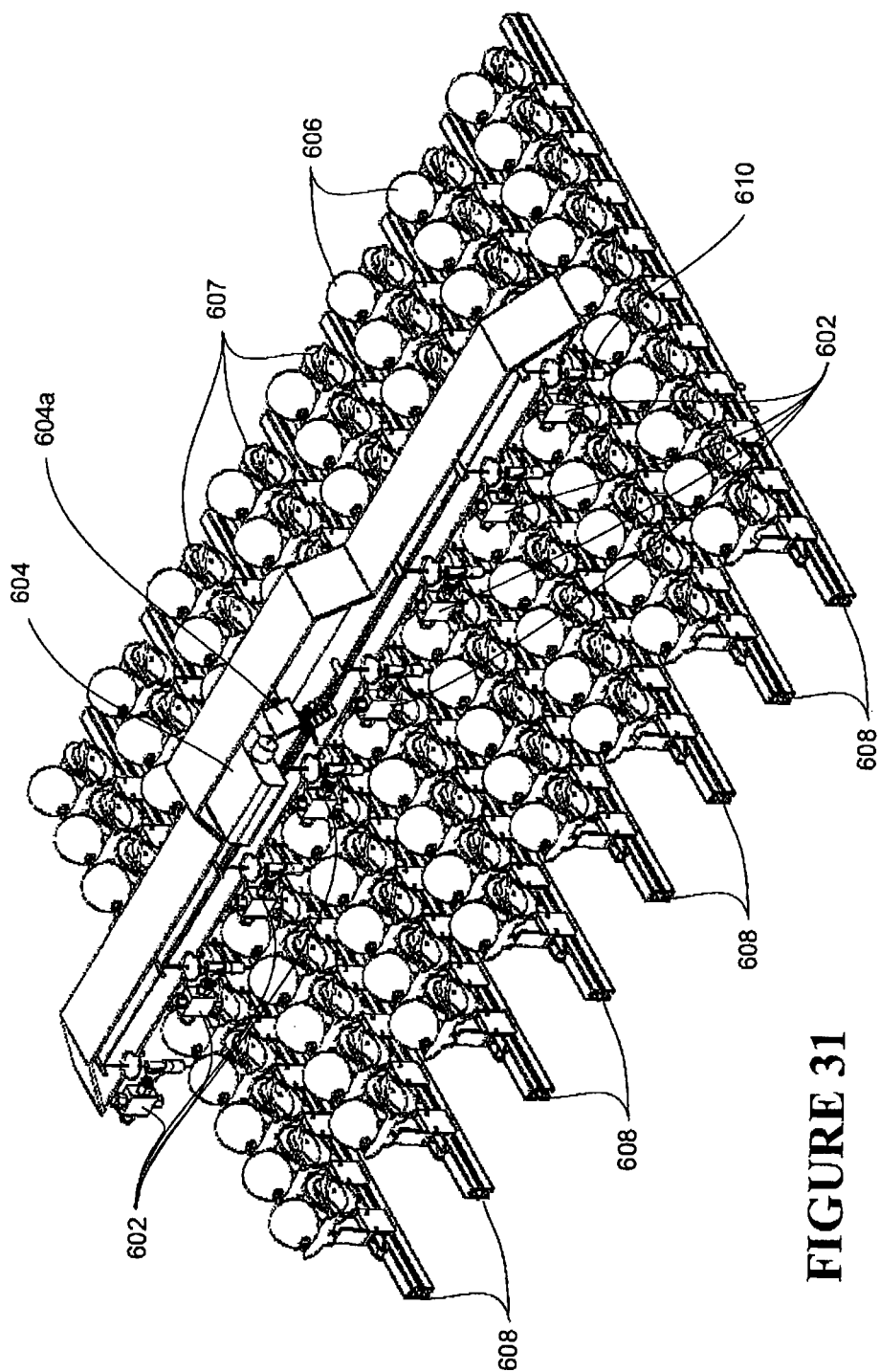
FIG. 31 shows a system of an alternative embodiment of the present invention with the guide of FIG. 29A and with multiple conveying lanes.
Figure 32:
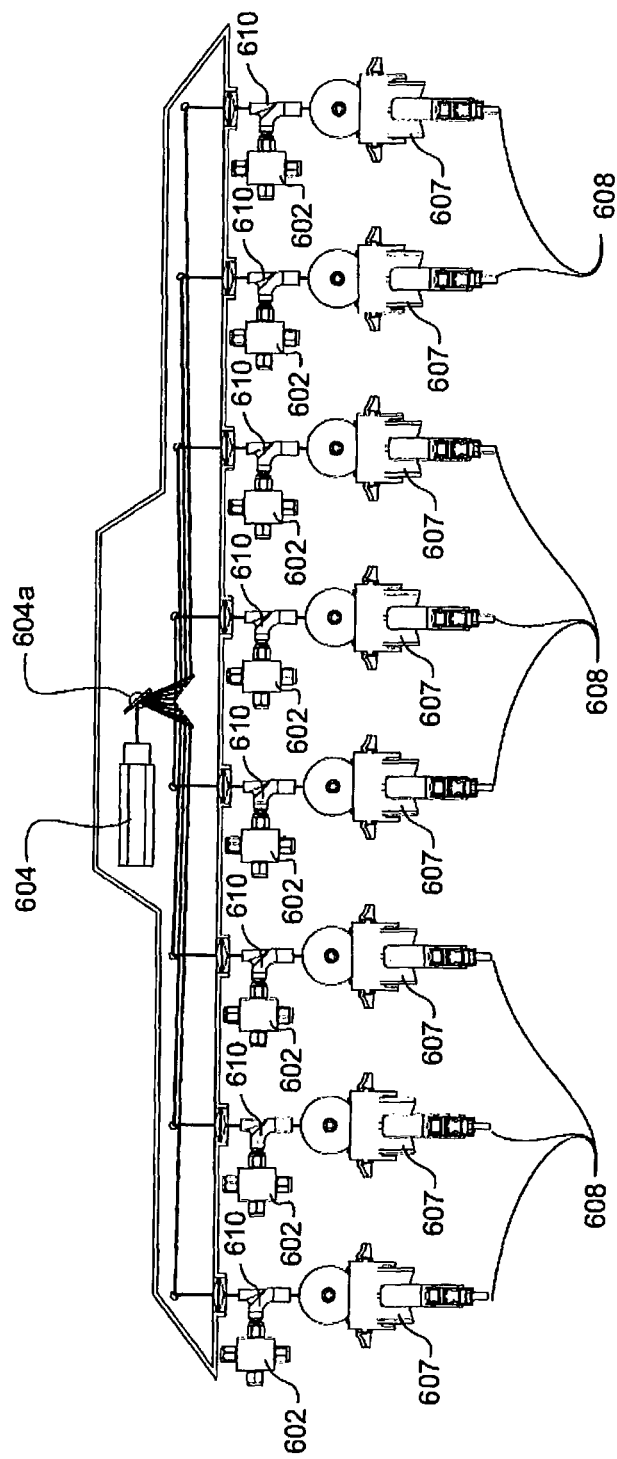
FIG. 32 shows an end view of the system of FIG. 31.

FIGS. 31 and 32 show an embodiment where an impulse guide 610 is used in a multiple-lane or conveyor system. The impulse guide 610 may be the impulse guide shown and described with reference to FIG. 29A or the impulse guide shown and described with reference to FIG. 30A for example. Similar to the embodiment shown in FIGS. 19 and 20, the detector 604 comprises an optical guide 604a for selectively communicating signals between the detector 604 and from the object 606 in one of the holders 607 on one of a plurality of conveyors 608. Similar to the embodiment described with reference to FIGS. 19 and 20, the optical guide 604a may be an electronically-moveable deflection mirror. Each conveyor 608 is adapted to convey a series of objects 606. In that setup, the system comprises a plurality of inducing arrangements 602 and a plurality of impulse guides 610. Each inducing arrangement 602 and each impulse guide 610 are assigned to one of the plurality of conveyors 608.

Results

The results of the Fluid Tap method using the system 600 described with reference to FIGS. 26 to 28, in which the inducing arrangement 602 comprises the second embodiment valve 400, will now be discussed with reference to FIGS. 33 to 35. The system 600 comprises the second embodiment impulse guide 800, the detector 604 and the processor P that have been described previously.

Figure 33:
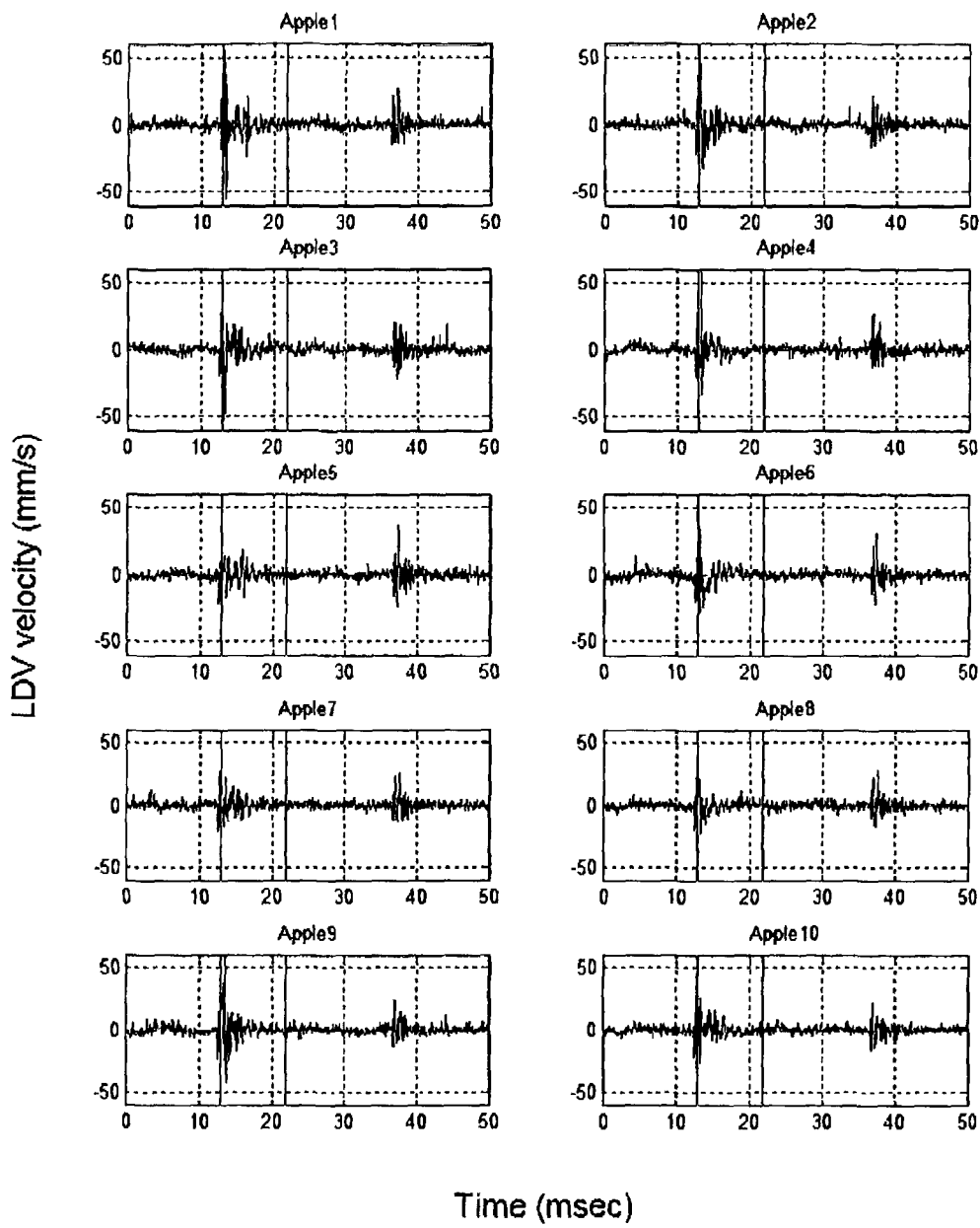
FIG. 33 shows an LDV recording of surface vibration of ten apples by an impulse of gas using a system of the second embodiment of the present invention.

FIG. 33 shows the LDV velocity spectra for ten apples from the Fluid Tap system where the direction of the impulse of gas from the inducing arrangement is substantially collinear with the signals between the detector and object. The conveyor is operated at 1 m/s, and the system is configured to determine the property of 10 fruit per second, with an air pressure of 2 MPa and an LDV velocity range setting of 0.1 m/s. The recording for each spectra is 50 milliseconds long, and shows two impulses on each fruit, at about 12 milliseconds and 36 milliseconds respectively. The vertical lines between 12 milliseconds and 22 milliseconds define a 10 millisecond window for determining the resonant response from the impulse.

Figure 34:
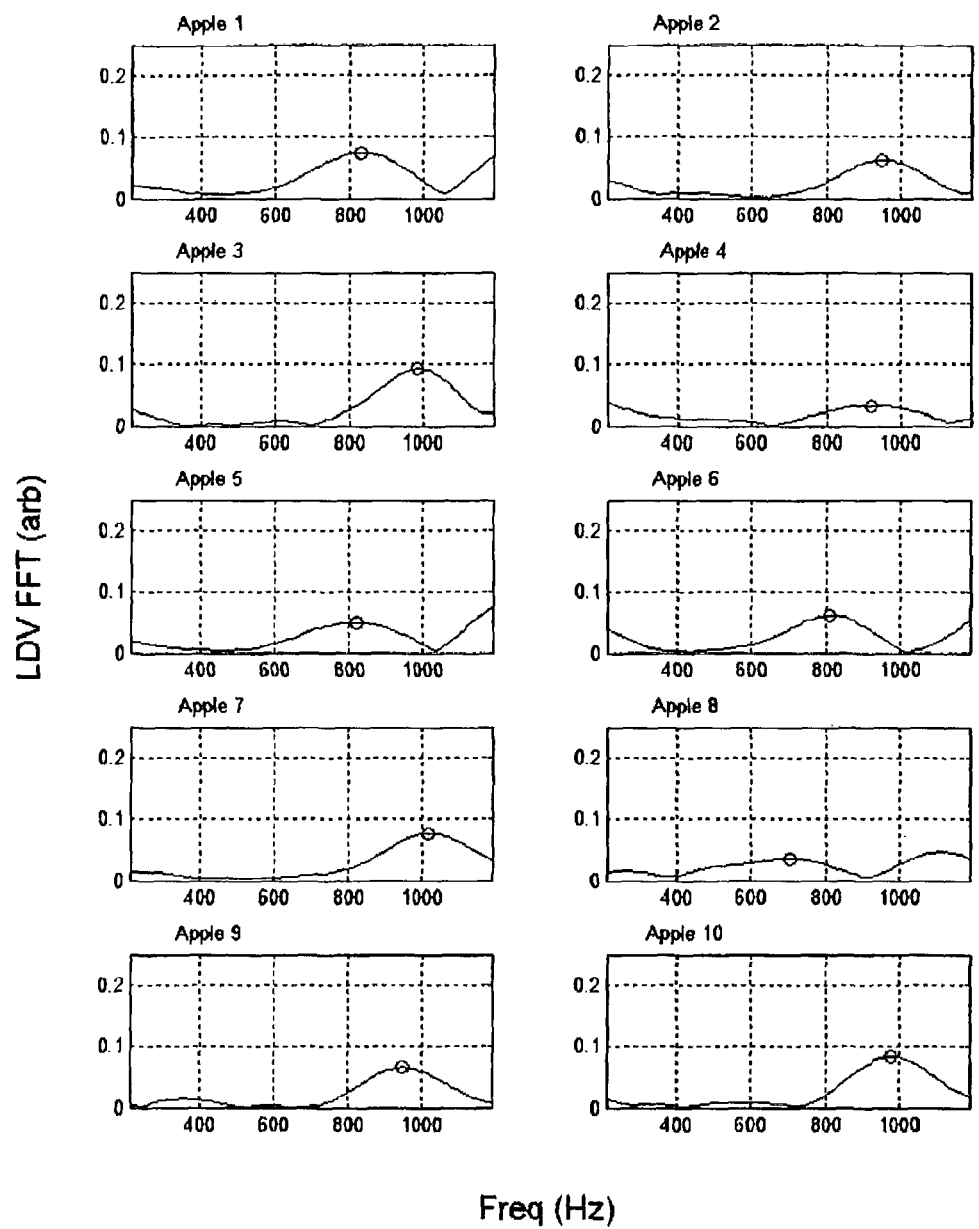
FIG. 34 shows the frequency spectra of the LDV recordings shown in FIG. 33 using the system of the second embodiment of the present invention.

FIG. 34 shows the frequency spectra generated from the first impulse during the 10-second window for each fruit shown in FIG. 33. The resonant peaks for the ten apples can be determined from the frequency spectra. The table below shows a comparison of the determined resonant peaks and the results using the Aweta method.

TABLE 2

A comparison of resonant frequencies for ten different apples using the Fluid Tap method and the Aweta method.

| | Peak resonant frequency (Hz) | |
|---|---|---|
| Apple | Using the Fluid Tap method | Using the Aweta method |
| 1 | 830.1 | 794.0 |
| 2 | 947.3 | 921.0 |
| 3 | 986.3 | 915.0 |
| 4 | 918.0 | 861.0 |
| 5 | 820.3 | 773.0 |
| 6 | 810.5 | 746.0 |
| 7 | 1016.0 | 966.0 |
| 8 | 703.1 | 659.0 |
| 9 | 947.3 | 918.0 |
| 10 | 976.6 | 956.0 |

Figure 35:
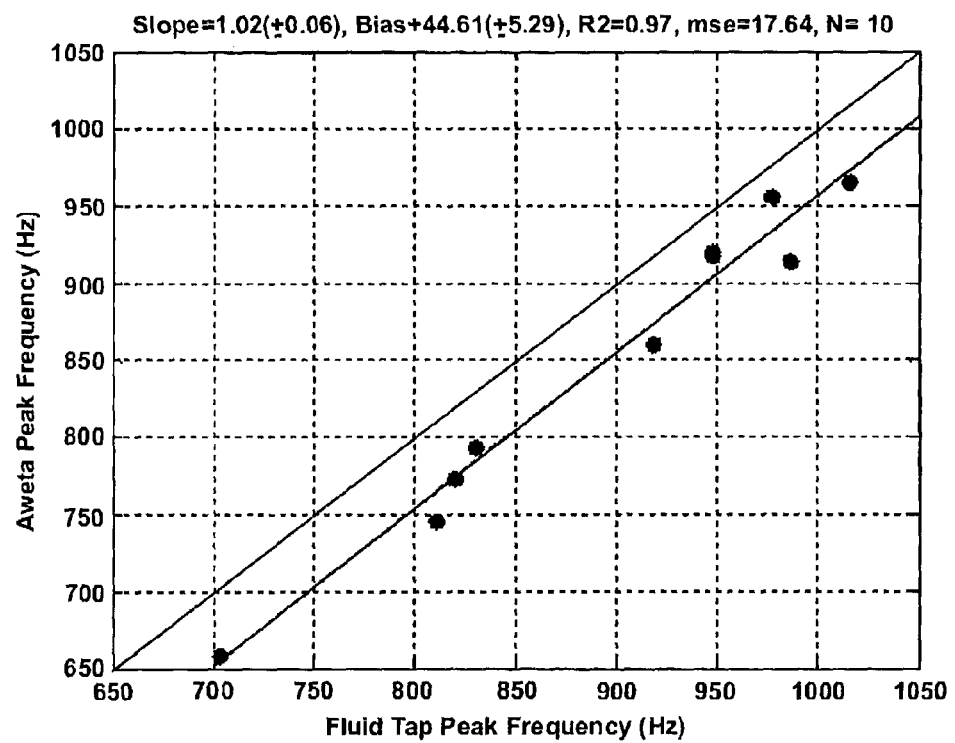
FIG. 35 shows the Peak Frequency relationships between Aweta measurements and measurements using the system of the second embodiment of the present invention for ten apples.

FIG. 35 shows the peak frequency relationships between measurements obtained from the Aweta system and measurements from the Fluid Tap system 600 for ten apples shown in Table 2. According to this Figure, there is a strong correlation between the results obtained using the Aweta method and the results obtained using the Fluid Tap method of the present invention.

The firmness of the object can be determined from these measurements of the Fluid Tap system. For example, firmer objects would generally have higher peak resonant frequencies.

Preferred embodiments of the invention have been described by way of example only and modifications may be made thereto without departing from the scope of the invention.

While specific components and parameters have been described, it will be appreciated that these could be varied while still working within the scope of the present invention.

The Fluid Tap concept suggests other similar techniques that could be used to provide non-contact stimuli for moving fruit. Besides the preferred embodiments of the inducing arrangement described above, other inducing arrangements may be used. For example, an automatic repeat mechanism such as that used in automatic paintball guns might be used or modified to provide rapidly repeating bursts of compressed air; or an explosive system, such as a hydrogen-oxygen ignition system or an adapted combustion engine could provide regular packets of percussive gasses.

Preferred embodiments of the valve have other applications where short pulses of gas or other fluid are required. For example, the valve may create the stimulus for generating a pressure wave in a material for stress-wave testing of objects, wherein the velocity of a travelling sound pulse in a material is measured and used to infer the physical condition, commonly the stiffness, of the material or object. Another example, the valve may be the core component of a depth gauge based on the pulse echo method (pulse reflected back from surface). The acoustic pulse might have advantages over standard pulse echo in some circumstances. For instance, the echo off a rough surface might be stronger, less attenuated and scattered than ultrasonic. Additionally, the repeated crack of the valve could be very loud and is machine-gun like, which is suitable for a crowd control device for crowd quietening or dispersal. The Fluid Tap method and system may be combined with a vision system for measuring shape and size and/or weight information (such as Compac's InVision system) to improve performance or to compensate for variations in the size and shape.

Other example modifications are described in the 'Summary of Invention' section.

The invention claimed is:

1. A system for determining a property of an object, the system comprising:
    an inducing arrangement for generating an impulse of fluid having a duration of less than about 5 milliseconds and for directing the impulse of fluid towards the object to induce a physical vibration of the object, wherein the inducing arrangement does not contact the object when inducing the vibration of the object;
    a detector for detecting the physical vibration of the object, wherein the detector does not contact the object when detecting the physical vibration of the object; and
    a processor coupled to the detector for determining the property of the object based on at least the detected physical vibration.

2. The system according to claim 1, wherein the inducing arrangement is a transmitter for transmitting the impulse of fluid that impinges a surface of the object thereby inducing the physical vibration of the object.

3. The system according to claim 1, wherein the inducing arrangement comprises a valve comprising:
    a housing having
        a bore,
        an inlet port, wherein fluid from a fluid source can be delivered into the bore through the inlet port, and
        an outlet port, wherein fluid from within the bore can be delivered through the outlet port; and
    a valve member moveable within the bore of the housing between a first substantially closed configuration, an open configuration, and a second substantially closed configuration, wherein in the open configuration, the valve member substantially allows fluid flow from the inlet port to the outlet port, and in the first and second substantially closed configurations, the valve member substantially restricts fluid flow from the inlet port to the outlet port, the valve member being moveable from one of the substantially closed configurations to the open configuration to the other substantially closed configuration in a single direction of motion of the valve member within the bore.

4. The system according to claim 3, wherein the valve member is a reciprocable spool valve member, and the spool valve member is moveable from one of the substantially closed configurations to the open configuration to the other substantially closed configuration in a single linear stroke of the spool valve member within the bore.

5. The system according to claim 4, wherein the spool valve member has two restricting sections, each restricting section being dimensioned to substantially restrict fluid flow from the inlet port to the outlet port when the spool valve member is in either of the substantially closed configurations, and a delivery section located in between the two restricting sections, the delivery section being dimensioned to substantially allow fluid flow from the inlet port to the outlet port when the spool valve member is in the open configuration.

6. The system according to claim 3, wherein the valve member is a rotatable spool valve member, and the rotatable spool valve member is moveable from one of the substantially closed configurations to the open configuration to the other substantially closed configuration in a single rotation of the rotatable spool valve member within the bore.

7. The system according to claim 3, wherein the inducing arrangement further comprises a driving arrangement for driving the valve member within the bore from one of the substantially closed configurations to the open configuration to the other substantially closed configuration.

8. The system according to claim 7 wherein the valve member is a reciprocable spool valve member, and the spool valve member is moveable from one of the substantially closed configurations to the open configuration to the other substantially closed configuration in a single linear stroke of the spool valve member within the bore, and wherein the spool valve member is pneumatically driven and the driving arrangement is a pneumatic valve connected to at least one end of the bore.

9. The system according to claim 7, wherein the driving arrangement comprises a solenoid.

10. The system according to claim 3, wherein the inducing arrangement is arranged to generate the impulse of fluid through the outlet port, the duration of the impulse corresponding to an amount of time the valve member remains in the open configuration during a stroke, and wherein the duration of the impulse of fluid is less than about 3 milliseconds.

11. The system according to claim 1, wherein the impulse of fluid has a direction of propagation towards the object substantially perpendicular to a direction of signals communicated between the detector and the object.

12. The system according to claim 1, wherein the impulse of fluid has a direction of propagation towards the object that is generally coincident to a direction of signals communicated between the detector and the object, wherein the direction of propagation and the direction of signals are generally coincident with each other on a top surface of the object.

13. The system according to claim 1, wherein the fluid is a gas, a liquid, a mixture of liquid and gas, or a mixture of gas and one or more powdered solids.

14. The system according to claim 1, wherein the detector comprises a laser-based detector.

15. The system according to claim 1, comprising a plurality of conveyors and a plurality of inducing arrangements, each inducing arrangement being assigned to one of the plurality of conveyors.

16. The system according to claim 1, wherein a direction of signals between the detector and the object is between about 89.5° and about 90.5° to a direction of movement of the object.

17. A method for determining a property of an object, the method comprising:
inducing by an inducing arrangement a physical vibration of the object, the inducing arrangement being configured to generate an impulse of fluid having a duration of less than about 5 milliseconds and to direct the impulse of fluid towards the object, wherein the inducing arrangement does not contact the object when inducing a vibration of the object;
detecting by a detector the physical vibration of the object, wherein the detector does not contact the object when detecting the vibration; and
determining the property of the object based on at least the detected physical vibration.

* * * * *